(12) United States Patent
Yang et al.

(10) Patent No.: US 12,084,487 B2
(45) Date of Patent: Sep. 10, 2024

(54) NANOPARTICLES HAVING MOLECULES THAT BIND OR BLOCK PD-L1 AND USES IN TREATING CANCER

(71) Applicant: Emory University, Atlanta, GA (US)

(72) Inventors: Lily Yang, Atlanta, GA (US); Erica Bozeman, North Wales, PA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 18/357,979

(22) Filed: Jul. 24, 2023

(65) Prior Publication Data

US 2023/0382971 A1 Nov. 30, 2023

Related U.S. Application Data

(63) Continuation of application No. 16/342,146, filed as application No. PCT/US2017/056810 on Oct. 16, 2017, now abandoned.

(60) Provisional application No. 62/408,141, filed on Oct. 14, 2016.

(51) Int. Cl.
| | |
|---|---|
| *C07K 14/705* | (2006.01) |
| *A61K 31/405* | (2006.01) |
| *A61K 31/4245* | (2006.01) |
| *A61K 31/7088* | (2006.01) |
| *A61K 38/00* | (2006.01) |
| *A61K 38/17* | (2006.01) |
| *A61K 38/48* | (2006.01) |
| *A61K 45/06* | (2006.01) |
| *A61K 47/62* | (2017.01) |
| *A61K 47/69* | (2017.01) |
| *A61K 49/00* | (2006.01) |
| *A61K 49/18* | (2006.01) |
| *A61K 51/08* | (2006.01) |
| *A61P 35/02* | (2006.01) |
| *C07K 14/47* | (2006.01) |
| *C07K 14/78* | (2006.01) |
| *G01N 33/574* | (2006.01) |
| *B82Y 5/00* | (2011.01) |

(52) U.S. Cl.
CPC ...... *C07K 14/70521* (2013.01); *A61K 31/405* (2013.01); *A61K 31/4245* (2013.01); *A61K 31/7088* (2013.01); *A61K 38/177* (2013.01); *A61K 38/482* (2013.01); *A61K 38/4886* (2013.01); *A61K 45/06* (2013.01); *A61K 47/62* (2017.08); *A61K 47/6929* (2017.08); *A61K 47/6939* (2017.08); *A61K 49/0002* (2013.01); *A61K 49/0093* (2013.01); *A61K 49/1866* (2013.01); *A61K 51/08* (2013.01); *A61P 35/02* (2018.01); *C07K 14/70596* (2013.01); *C12Y 304/21073* (2013.01); *C12Y 304/2408* (2013.01); *G01N 33/574* (2013.01); *B82Y 5/00* (2013.01); *C07K 2319/21* (2013.01)

(58) Field of Classification Search
CPC .......... C07K 14/70521; A61K 31/7088; A61K 38/177; A61K 47/62; A61K 47/6929; A61P 35/02
See application file for complete search history.

(56) References Cited

U.S. PATENT DOCUMENTS

| | | | |
|---|---|---|---|
| 2012/0121634 | A1 | 5/2012 | Chen |
| 2012/0328693 | A1 | 12/2012 | Lan |
| 2013/0343996 | A1 | 12/2013 | Lee |
| 2015/0087581 | A1 | 3/2015 | Sasikumar |

FOREIGN PATENT DOCUMENTS

| | | |
|---|---|---|
| CN | 103304638 | 12/2014 |
| WO | 2012031205 | 3/2012 |

OTHER PUBLICATIONS

UnitProt Accession No. Q02242, accessed May 5, 2024 at URL uniprot.org/uniprotkb/Q02242.txt, pp. 1-6 (Year: 2024).*
GenBank Accession No. KJ865857, accessed May 5, 2024 at URL https://www.ncbi.nlm.nih.gov/nuccore/KJ865857, 1 page. (Year: 2024).*
Bozeman et al. Abstract A60: Synergistic effect of targeted chemotherapy delivery using theranostic nanoparticles and PD-L1 blockade in an orthotopic mouse pancreatic cancer model, Cancer Immunol Res Oct. 2015 3; A60.
Cerny et al. The Role of CXCR3/Ligand Axis in Cancer, International Trends in Immunity vol. 3 No. 2, 2015.
Chen et al. Preclinical evaluation of a urokinase plasminogen activator receptor-targeted nanoprobe in rhesus monkeys, International Journal of Nanomedicine 2015:10 6689-6698.
Huang et al. Casein-coated Iron Oxide Nanoparticles for High MRI Contrast Enhancement and Efficient Cell Targeting, ACS Appl Mater Interfaces. 2013, 5(11): 4632-4639.
Lazarus et al., Abstract 3209: CRLX101, an investigational nanoparticle-drug conjugate of campothecin, demonstrates synergy with immunotherapy agents in preclinical models, Cancer Res, 2016, 76 (Sup14):3209.
Lee et al., Theranostic Nanoparticles with Controlled Release of Gemcitabine for Targeted Therapy and MRI of Pancreatic Cancer, ACS Nano. 2013, 7(3): 2078-2089.
Nielsen et al. Stromal cells associated with early invasive foci in human mammary ductal carcinoma in situ coexpress urokinase and urokinase receptor, Int. J. Cancer: 120, 2086-2095 (2007).
Qiu et al. Regulating Immunity and Inhibiting Tumor Growth by the Recombinant Peptide sPD-1-CH50, Anticancer Research 29: 5089-5094 (2009).

(Continued)

*Primary Examiner* — Julie Ha
*Assistant Examiner* — Kristina M Hellman
(74) *Attorney, Agent, or Firm* — Emory Patent Group

(57) ABSTRACT

This disclosure relates to peptides and nanoparticles comprising a surface molecule that binds or blocks PD-L1. In certain embodiments, the disclosure relates to methods of using peptides or nanoparticles disclosed herein for the treatment of cancer. In certain embodiments, the disclosure relates to methods of using nanoparticles disclosed herein for therapeutic and diagnostic applications.

4 Claims, 10 Drawing Sheets

Specification includes a Sequence Listing.

(56) References Cited

OTHER PUBLICATIONS

Saldano et al. Evolutionary Conserved Positions Define Protein Conformational Diversity, PLoS Comput Biol, 201512(3): e1004775.
Veiseh et al. Optical and MRI Multifunctional Nanoprobe for Targeting Gliomas, Nano Lett., vol. 5, No. 6, 2005, 1003-1008.
Yang, Single Chain Epidermal Growth Factor Receptor Antibody Conjugated Nanoparticles for in vivo Tumor Targeting and Imaging, Small, 2009, 5(2): 235-243.
Yang et al. Receptor-Targeted Nanoparticles for In vivo Imaging of Breast Cancer, Clin Cancer Res, 2009,15(14):4722.
Yang et al. Theranostic Nanoparticles Carrying Doxorubicin Attenuate Targeting Ligand Specific Antibody Responses Following Systemic Delivery, Theranostics, 2015, 5(1): 43-61.
Zak et al. Structure of the Complex of Human Programmed Death 1, PD-1, and Its Ligand PD-L1, Structure, 2015, 23, 2341-2348.
Zhou et al. IGF1 Receptor Targeted Theranostic Nanoparticles for Targeted and Image-Guided Therapy of Pancreatic Cancer, ACS Nano. 2015, 9(8): 7976-7991.

\* cited by examiner

PD-1 protein partial sequence and PD-1 like peptide location:
61
ESFVL<u>NWYRM</u> <u>SPSNQTDKLA AFPEDRSQPG</u> QDCRFRVTQL (SEQ ID NO: 10)
      NWNRL SPSNQTEKQAAP (SEQ ID NO: 8)

140
PNGRDFHMSV VRARRNDSGT <u>YLCGAISLAP KAQIKE</u>SLRA
(SEQ ID NO: 11)
                        (SEQ ID NO: 9) CGAISLHPKAKIEE

FIG. 1A

PD-1 (Y) – NWNRLSPSNQTEKQAAPHHHHCGAISLHPKAKIEE
(SEQ ID NO: 2)
PD-1(Lin) – NWNRLSPSNQTEKQAACGAISLHPKAKIEESPGHHHH
(SEQ ID : NO: 3)

FIG. 1B

NANOPARTICLES HAVING MOLECULES THAT BIND OR BLOCK PD-L1 AND USES IN TREATING CANCER

CROSS-REFERENCE TO RELATED APPLICATIONS

This application is a continuation of U.S. application Ser. No. 16/342,146 filed Apr. 15, 2019, which is the National Stage of International Application No. PCT/US2017/056810 filed Oct. 16, 2017, which claims the benefit of U.S. Provisional Application No. 62/408,141 filed Oct. 14, 2016. The entirety of each of these applications is hereby incorporated by reference for all purposes.

STATEMENT REGARDING FEDERALLY FUNDED RESEARCH

This invention was made with government support under CA202846, CA154129, CA151810, and CA189633 awarded by the National Institutes of Health. The government has certain rights in the invention.

INCORPORATION-BY-REFERENCE OF MATERIAL SUBMITTED AS AN XML FILE VIA THE OFFICE ELECTRONIC FILING SYSTEM

The Sequence Listing associated with this application is provided in XML, format and is hereby incorporated by reference into the specification. The name of the XML file containing the Sequence Listing is 16049USCON.xml. The XML file is 31 KB, was created on Jul. 12, 2023, and is being submitted electronically via the USPTO patent electronic filing system.

BACKGROUND

Cancer treatment is typically approached by a combination of surgery along with chemotherapy and/or radiation. These approaches often neglect to eliminate completely small metastatic tumors. PD-L1 is expressed in tumor cells and tumor associated stromal cells, such as fibroblasts and macrophages. Preclinical and clinical studies have investigated the efficacy of monoclonal antibody therapies that act as immune checkpoint blockades in multiple cancer types. FDA approval of immune checkpoint blocking related therapeutic antibodies include ipilimumab (anti-CTLA-4) for melanoma, nivolumab (anti-PD-1) for melanoma, non-small cell lung cancer (NSCLC) and renal cell carcinoma RCC, and pembrolizumab (anti-PD-1) for melanoma and NSCLC. Several cancers including pancreatic cancer are generally non-responsive to these therapies. Thus, there remains a need to develop improved therapeutic approaches.

Bozeman et al. report targeted chemotherapy delivery using theranostic nanoparticles and PD-L1 blockade in an orthotopic mouse pancreatic cancer model. In: Proceedings of the AACR Special Conference: Tumor Immunology and Immunotherapy: A New Chapter; Dec. 1-4, 2014; Orlando, FL. Philadelphia (PA): AACR; Cancer Immunol Res 2015; 3(10 Suppl):Abstract nr A60. See also Zhou et al. IGF1 Receptor Targeted Theranostic Nanoparticles for Targeted and Image-Guided Therapy of Pancreatic Cancer. ACS Nano, 2015, 9(8):7976-91. Bombelli et al. Nanoparticle therapies for future metastatic melanoma treatment. Lancet Oncol. 2014, 15(1):e22-32. Yang E, et al. Theranostic Nanoparticles Carrying Doxorubicin Attenuate Targeting Ligand Specific Antibody Responses Following Systemic Delivery. Theranostics, 2015, 5(1):43-61. Huang J, et al. Casein-coated Iron Oxide Nanoparticles for High MRI Contrast Enhancement and Efficient Cell Targeting. ACS applied materials & interfaces, 2013, 5(11):4632-4639. Lee G Y, et al. Theranostic Nanoparticles with Controlled Release of Gemcitabine for Targeted Therapy and MRI of Pancreatic Cancer. ACS nano, 2013, 7(3):2078-2089. See WO 2012/031205, WO 2013/0343996, CN103304638.

References cited herein are not an admission of prior art.

SUMMARY

This disclosure relates to nanoparticles comprising a surface molecule that binds or blocks PD-L1. In certain embodiments, this disclosure relates to methods of using peptides or nanoparticles disclosed herein for the treatment of cancer. In certain embodiments, this disclosure relates to methods of using nanoparticles disclosed herein for therapeutic and diagnostic applications.

In certain embodiments, the molecule that binds or blocks PD-L1 is a peptide comprising or consisting of NWNRLSPSNQTEKQAAP (SEQ ID NO: 8) or variants thereof and/or CGAISLHPKAKIEE (SEQ ID NO: 9) or variants thereof. In certain embodiments, the molecule that binds or blocks PD-L1 is a peptide comprising or consisting of NWYRMSPSNQTDKLAA (SEQ ID NO: 12) or variants thereof and/or CGAISLAPKAQIKE (SEQ ID NO: 13) or variants thereof.

In certain embodiments, the variant of SEQ ID NO: 8 has at least 70, 80, 85, 90, or 95% percent sequence identity. In certain embodiments, the variant of SEQ ID NO: 8 has up to 1 or 2 or 3 amino acid substitutions, deletions, and/or additions. In certain embodiments, the variant of SEQ ID NO: 9 has at least 80, 85, 90, or 95% percent sequence identity. In certain embodiments, the variant of SEQ ID NO: 9 has up to 1 or 2 amino acid substitutions, deletions, and/or additions.

In certain embodiments, the variant of SEQ ID NO: 12 has at least 70, 80, 85, 90, or 95% percent sequence identity. In certain embodiments, the variant of SEQ ID NO: 12 has up to 1 or 2 or 3 amino acid substitutions, deletions, and/or additions. In certain embodiments, the variant of SEQ ID NO: 13 has at least 80, 85, 90, or 95% percent sequence identity. In certain embodiments, the variant of SEQ ID NO: 13 has up to 1 or 2 amino acid substitutions, deletions, and/or additions.

In certain embodiments, the molecule that binds or blocks PD-L1 is a peptide comprising or consisting of SEQ ID NO: 1, 2, 3 or variants thereof.

In certain embodiments, this disclosure relates to targeted delivery of nanoparticles into tumors mediated by PD-L1 blocking peptides. In certain embodiments, this disclosure contemplates nanoparticles comprising PD-1 peptides or fragments or PD-1 like peptides with dual binding domains that are fusions with a poly-histidine tag or other heterologous peptide. The peptides may be conjugated to the nanoparticles through affinity interaction with NTA-Cu that is covalently linked to an outer polymer, configured to form ligand-metal complexes with the poly-histidine tag. The peptides may be conjugated to the nanoparticles through an outer polymer covalently linked to NTA and a metal configured to form ligand-metal complexes with the poly-histidine tag.

In certain embodiments, this disclosure contemplates targeted delivery of PD-L1 blocking peptides, such as those comprising or consisting of SEQ ID NO: 8 or variants and/or SEQ ID NO: 9 or variants, such as SEQ ID NO: 1, 2, 3, or variants, into tumors to reduce potential systemic effects of blocking the PD-1 and PD-L1 interaction on the regulation of normal immune responses.

In certain embodiments, this disclosure contemplates methods of treating cancer comprising administering an effective amount of a peptide disclosed herein or a nanoparticle comprising a surface peptide disclosed herein such as those comprising or consisting of SEQ ID NO: 8 or variants and/or SEQ ID NO: 9 or variants, such as SEQ ID NO: 1, 2, 3, or variants in combination with a nanoparticle comprising an amino-terminal fragment (ATF) of uPA wherein the nanoparticle optionally further comprise a chemotherapy agent to a subject in need thereof. In certain embodiments, the components are on a single particle or are contained on two particles, e.g., a first nanoparticle comprising a surface peptide such as those comprising or consisting SEQ ID NO: 8 or variants and/or SEQ ID NO: 9 or variants, such as SEQ ID NO: 1, 2, 3, or variants and a second nanoparticle comprising an amino-terminal fragment (ATF) of uPA or ATF-MMP14 catalytic domain fusion peptide further comprising a chemotherapy agent. ATF-Matrix MetalloProtease 14 (MMP14) can be used to break tumor stromal barrier so that the PD1-like peptide conjugated nanoparticles can be delivered into tumor center and bind to PDL-1 expressing tumor and stromal cells. In certain embodiments, nanoparticles disclosed herein comprise or consist of SEQ ID NO: 8 or variants and/or SEQ ID NO: 9 or variants, such as SEQ ID NO: 1, 2, 3, or variants and further comprises the amino-terminal fragment (ATF) of uPA or ATF-MMP14 on the outer surface of the particle.

In certain embodiments, the components are on a single particle or are contained on two particles, e.g., a first nanoparticle comprising a surface peptide comprising or consisting of SEQ ID NO: 8 or variants and/or SEQ ID NO: 9 or variants, such as SEQ ID NO: 1, 2, 3, or variants and a second nanoparticle comprising an amino-terminal fragment (ATF) of uPA further comprising a chemotherapy agent. In certain embodiments, nanoparticles disclosed herein comprise a peptide such as those comprising or consisting of SEQ ID NO: 8 or variants and/or SEQ ID NO: 9 or variants, such as SEQ ID NO: 1, 2, 3, or variants and further comprise the amino-terminal fragment (ATF) of uPA on the outer surface of the particle.

In certain embodiments, variants of NWNRLSPSNQTEKQAAP (SEQ ID NO: 8) are selected from NWNRMSPSNQTEKQAAP (SEQ ID NO: 14), NWNRMSPSNQTDKQAAP (SEQ ID NO: 15), NWNRMSPSNQTDKLAAP (SEQ ID NO: 16), NWNRLSPSNQTEKLAAP (SEQ ID NO: 17), NWNRLSPSNQTDKLAAP (SEQ ID NO: 18), NWYRMSPSNQTEKQAAP (SEQ ID NO: 19), NWYRMSPSNQTDKQAAP (SEQ ID NO: 20), NWYRMSPSNQTDKLAAP (SEQ ID NO: 21), NWYRLSPSNQTEKLAAP (SEQ ID NO: 22), and NWYRLSPSNQTDKLAAP (SEQ ID NO: 23).

In certain embodiments, variants of CGAISLHPKAKIEE (SEQ ID NO: 9) are selected from CGAISLAPKAKIEE (SEQ ID NO: 24), CGAISLAPKAQIEE (SEQ ID NO: 25), CGAISLAPKAQIKE (SEQ ID NO: 13), CGAISLHPKAKIKE (SEQ ID NO: 27), and CGAISLHPKAQIKE (SEQ ID NO: 28).

In certain embodiments, this disclosure contemplates a peptide comprising NWYRMSPSNQTDKLAAPXXXXCGAISLAPKAQIKE (SEQ ID NO: 29), NWYRMSPSNQTDKLAAPXXXCGAISLAPKAQIKE (SEQ ID NO: 30), NWYRMSPSNQTDKLAAPXXXXXCGAISLAPKAQIKE (SEQ ID NO: 31) or variants wherein each X is individually and independently at each occurrence any amino acid, histidine, or glycine.

In certain embodiments, this disclosure relates to a nucleic acid sequence that encodes a peptide disclosed herein. In further embodiments, this disclosure relates to a vector comprising a nucleic acid sequence that encodes a peptide disclosed herein. In certain embodiments, this disclosure relates to a cell comprising a vector comprising a nucleic acid sequence that encodes a peptide disclosed herein. In certain embodiments, this disclosure relates to an expression system comprising a vector comprising a nucleic acid sequence that encodes a peptide disclosed herein.

In certain embodiments, this disclosure relates to the isolated peptide comprising or consisting of any of the sequences disclosed herein such as SEQ ID NO: 1, 2, or 3 or variant, wherein the variant has at least 45, 50, 55, 60, 65, 70, 75, 80, 85, 90, 92, 95, 98 percent sequence identity or similarity. In certain embodiments, the variant has one or more or up to 1, 2, 3, 4, 5, 6, or 7 amino acid substitutions, deletions, and/or additions. In certain embodiments, the substitution is a conserved substitution. In certain embodiments, this disclosure relates to the peptide variant of SEQ ID NO: 1 that is capable of binding or blocking PD-L1.

In certain embodiments, this disclosure contemplates that the peptide disclosed herein comprises or consists of amino acid sequences, or N-terminal or C-terminal amino acid sequences, disclosed herein such that the amino acids in the sequence are less than 150, 100, or 50 amino acids. In certain embodiments, this disclosure contemplates that the peptide disclosed herein comprises or consists of amino acid sequences, or N-terminal or C-terminal amino acid sequences, disclosed herein such that the amino acids in the sequence are less than 45 or 40 or 35 amino acids.

In certain embodiments, this disclosure relates to a nanoparticle comprising a peptide disclosed herein wherein the nanoparticle comprises 20 to 30 or 10 to 40 or 10 to 60 or 10 to 100 of the peptide moieties bound to the exterior of the particle. In certain embodiments, the nanoparticle comprises copper-nitrilotriacetate complexes (NTA-Cu) and the peptide comprises a poly-histidine sequence wherein the peptide is bound to the particle by a complex of the poly histidine and copper complex. In certain embodiments, this disclosure relates to a nanoparticle comprising a core comprising metallic nanoparticles, such as iron oxide, gold, or silver, or polymeric nanoparticles. In certain embodiments, the core has an average diameter of 3 to 200 nm. In certain embodiments, the core has an average diameter of 4 to 10 or 3 to 20 or 3 to 50 nm.

In certain embodiments, nanoparticles disclosed herein further comprise conjugated ATF or ATF-MMP14 and/or a chemotherapy agent. In certain embodiments, nanoparticles disclosed herein further comprise an indoleamine-2,3-dioxygenase (IDO) inhibitor such as indoximod or epacadostat.

In certain embodiments, this disclosure relates to a pharmaceutical composition comprising a peptide disclosed herein or a nanoparticle disclosed herein and a pharmaceutically acceptable excipient. In further embodiments, this disclosure relates to a pharmaceutical composition in the form of an aqueous phosphate buffer solution. In certain embodiments, this disclosure relates to a pharmaceutical composition in the form of a pill, capsule, tablet, cream, or aerosol.

In certain embodiments, this disclosure relates to a method of treating cancer comprising administering an effective amount of a peptide disclosed herein or a nanoparticle comprising a peptide disclosed herein, e.g., a peptide such as those comprising SEQ ID NO: 8 or variants and/or SEQ ID NO: 9 or variants, such as SEQ ID NO: 1, 2, 3, or variants, to a subject in need thereof.

In certain embodiments, this disclosure relates to a method of treating cancer comprising administering an effective amount of a peptide disclosed herein or a nanoparticle comprising a peptide disclosed herein, e.g., a peptide such as those comprising SEQ ID NO: 12 or variants and/or SEQ ID NO: 13 or variants, such as SEQ ID NO: 1, 2, 3, or variants, to a subject in need thereof.

In certain embodiments, the cancer is mediated by PD-L1. In certain embodiments, the cancer is selected from carcinoma, lymphoma, blastoma, sarcoma, and leukemia, non-small cell lung, squamous cell, small-cell lung, peritoneum, hepatocellular, gastrointestinal, pancreatic, glioma, cervical, ovarian, liver, bladder, hepatoma, breast, colon, colorectal, endometrial or uterine, salivary gland, kidney, liver, prostate, vulval, thyroid, hepatic, leukemia and other lymphoproliferative disorders, and various types of head and neck. In certain embodiments, the cancer can be primary or metastatic tumors.

In further embodiments, this disclosure relates to methods of treating cancer further comprising administering a second nanoparticle and/or chemotherapy agent, additional immunomodulators, or indoleamine 2,3-dioxygenase (IDO) inhibitors, to the subject.

In certain embodiments, this disclosure relates to a method for cancer diagnosis comprising administering an effective amount of a peptide disclosed herein or nanoparticle disclosed herein to a subject in need thereof and detecting the particle about the area of a cancerous cell or tumor.

BRIEF DESCRIPTION OF THE DRAWINGS

FIG. 1A illustrates PD-1 protein partial sequences (SEQ ID NO: 10 and SEQ ID NO: 11) and two domains in the PD-1 like peptide having SEQ ID NO: 8 and SEQ ID NO: 9.

FIG. 1B illustrates two PD-1 like peptides. Peptide PD-1 (Y) has SEQ ID NO: 2. Peptide PD-1 (Lin) has SEQ ID NO: 3.

DETAILED DESCRIPTION

Figure 2:
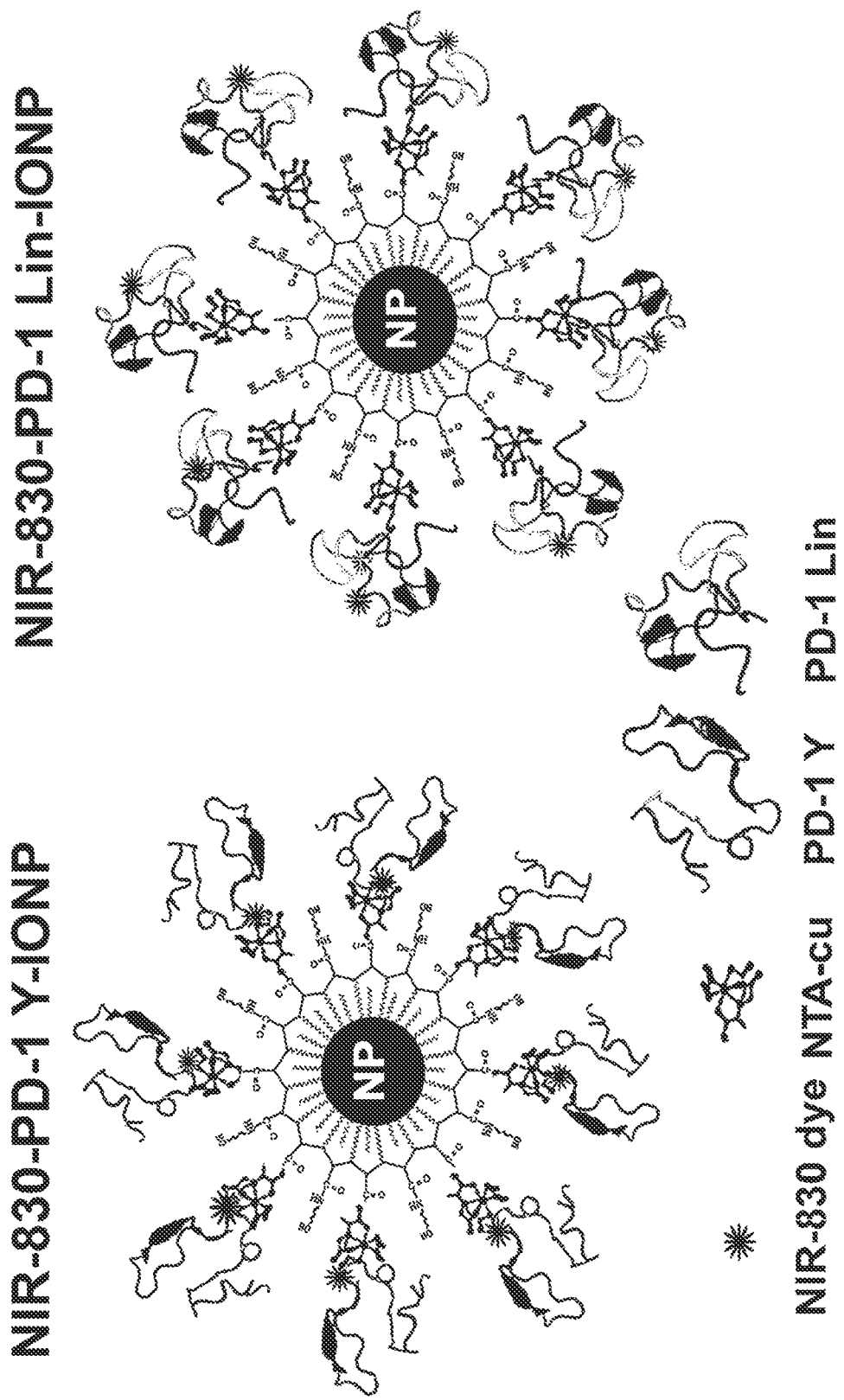
FIG. 2 illustrates the PD-1 like peptides conjugated to polymeric coated nanoparticle (NP).
Figure 3A:
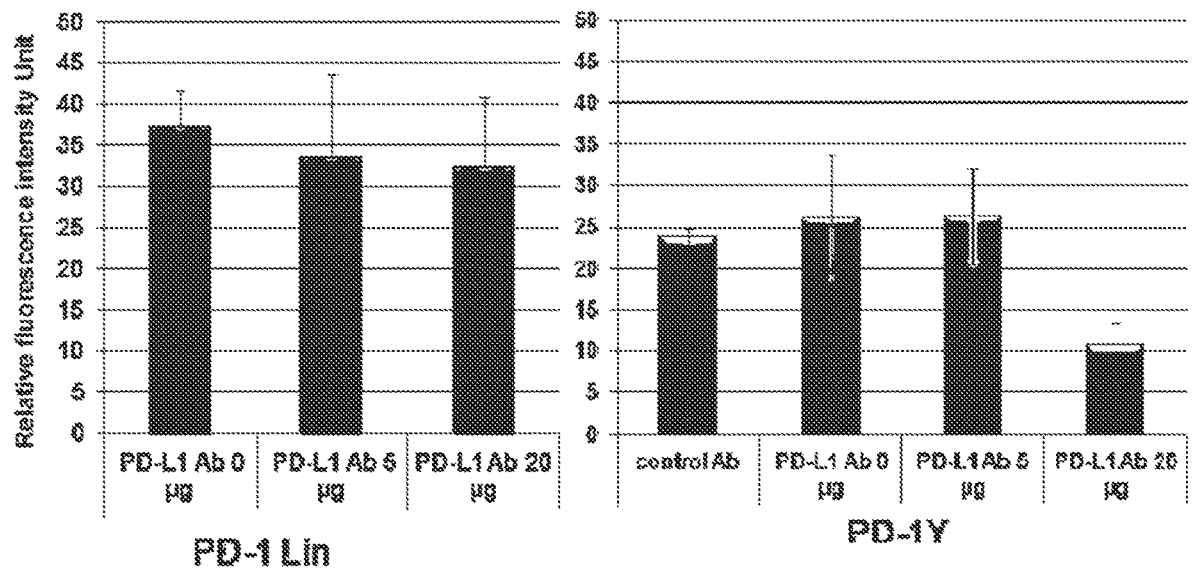
FIG. 3A shows data from a competition-binding assay. Two (2) μg of FITC labeled PD-1 peptides were mixed with 0, 5, 20 μg of anti-mouse PD-L1 antibody and then incubated with the KC cells for 2 hours. Unbound peptides and antibodies were washed off. Relative fluorescent intensities of KC cells were measured for each group.
Figure 3B:
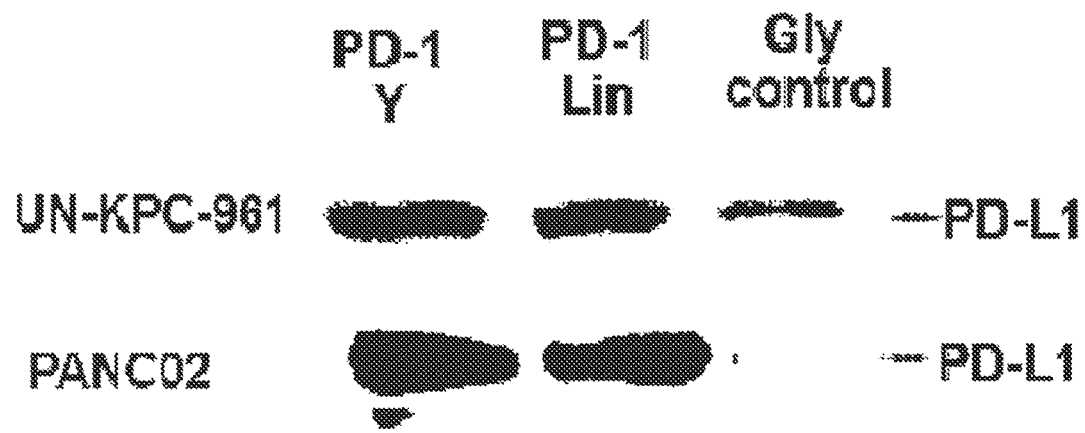
FIG. 3B shows data from a PD-1 peptide pull-down assay. PD-1 Lin or PD-1 Y peptides were conjugate to NTA-Ni beads and added to tumor cell lysates for 2 to 3 hrs. The beads were spin-down recovered. Protein fractions from the beads was examined by Western blot to identify PD-L1 proteins that were pulled down by the PD-1 peptides.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide. The term "consisting of" in reference to a peptide having an amino acid sequence refers a peptide having the exact number of amino acids in the sequence and not more or having not more than a range of amino acids specified in the claim. In certain embodiments, this disclosure contemplates that the "N-terminus of a peptide consists of an amino acid sequence," which refers to the N-terminus of the peptide having the exact number of amino acids in the sequence and not more or having not more than a range of amino acids specified in the claim; however, the C-terminus may be connected to additional amino acids, e.g., as part of a larger peptide. Similarly, this disclosure contemplates that the "C-terminus of a peptide consists of an amino acid sequence," which refers to the C-terminus of the peptide having the exact number of amino acids in the sequence and not more or having not more than a range of amino acids specified in the claim; however, the N-terminus may be connected to additional amino acids, e.g., as part of a larger peptide.

The term "nanoparticle" refers to a molecular conglomerate of between 1 and 1000 nm in diameter. One more molecules or biomolecules linked to the nanoparticle typically refers to covalently attaching the molecules or biomolecules to a polymer based exterior or coating. Within certain embodiment, the compositions and methods disclosed herein may be utilized with a variety of polymer-coated particle such as, e.g., quantum dots (QDs), metal particles, gold, silver, iron, and iron-oxide nanoparticles (IONPs).

"PD-L1" refers to programmed death-ligand 1, also known as CD274 and B7H1. The amino acid sequence of full-length PD-L1 is provided in GenBank as accession number NP_054862.1. PD-L1 is a 290 amino acid protein with extracellular IgV-like and IgC-like domains (amino acids 19-239 of full length PD-L1), a transmembrane domain and an intracellular domain of approximately 30 amino acids. PD-L1 is constitutively expressed on many cells such as antigen presenting cells (e.g., dendritic cells, macrophages, and B-cells) and on hematopoietic and non-hematopoietic cells (e.g., vascular endothelial cells, pancreatic islets, and sites of immune privilege). PD-L1 is also expressed on a wide variety of tumors, and virally-infected cells and is a component of the immunosuppressive milieu (Ribas 2012, NEJM 366: 2517-2519). PD-L1 binds to one of two T-cell co-inhibitors PD-1 and B7-1.

"PD-1" refers to the programmed death-1 protein, a T-cell co-inhibitor, also known as CD279. The amino acid sequence of full-length human PD-1 is provided in GenBank as accession number NP 005009.2 (SEQ ID NO: 1) MQIPQAPWPVVWAVLQLGWRPGWFLDSPDRPWN-PPTFSPALLVVTEGDNATFTCSFSNTSESFVLNWYR-MSPSNQTDKLAAFPEDRSQPGQDCRFRVTQLPNGR-DFHMSVVRARRN DSGTYLCGAISLAPKAQIKESLR-AELRVTERRAEVPTARPSPSPRPAGQFQTLVVGVVGG LLGSLVLLVWVLAVICSRAARGTIGARRTGQPL-KEDPSAVPVFSVDYGELDFQWREKTP EPPVPCVPE-QTEYATIVFPSGMGTSSPARRGSADGPRSAQPLR-PEDGHCSWPL. PD-1 is a member of the CD28/CTLA-4/ICOS family of T-cell co-inhibitors. PD-1 is a 288-amino acid protein with an extracellular N-terminal domain, which is IgV-like, a transmembrane domain and an intracellular domain containing an immunoreceptor tyrosine-based inhibitory (ITIM) motif and an immunoreceptor tyrosine-based switch (ITSM) motif (Chattopadhyay et al 2009, Immunol. Rev.). The PD-1 receptor has two ligands, PD-L1 and PD-L2.

An "isolated" peptide refers a peptide wherein its sequence was synthesized chemically or by recombinant techniques and purified/isolated after synthesis. The peptide sequence is not purified from naturally occurring environment but may be derived from genetically modified cells or plants, or by chemical synthesis.

A "specific binding" refers to binding by molecules, such as polynucleotides, antibodies, and other ligands, that are able to bind to or recognize a binding partner (or a limited number of binding partners) to a substantially higher degree than to other, similar biological entities.

A "subject" is defined to include any living animal or human. The term "non-human animal" includes all vertebrates, e.g., mammals and non-mammals, such as non-human primates, sheep, dog, cow, chickens, amphibians, reptiles, etc. A subject or non-human animal is "treated" if one or more beneficial or desired results, including desirably clinical results, are obtained. For purposes of this disclosure, beneficial or desired clinical results include, but are not limited to, one or more of the following: decreasing one or more symptoms resulting from the disease, increasing the quality of life of those suffering from the disease, decreasing the dose of other medications required to treat the disease, delaying the progression of the disease, and/or prolonging survival of individuals.

A "nucleic acid," or "oligonucleotide," is defined as a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide can be, for example, ribose sugars (a "ribonucleic acid," or "RNA"), or deoxyribose sugars (a "deoxyribonucleic acid," or "DNA"). In some cases, the polymer can comprise both ribose and deoxyribose sugars. Examples of bases include, but not limited to, the naturally occurring bases (e.g., adenosine or "A," thymidine or "T," guanosine or "G," cytidine or "C," or uridine or "U"). In some cases, the polymer can also comprise nucleoside analogs (e.g., azacytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitropyrrole, 4-methylindole, 4-thiouridine, 4-thiothymidine, 2-aminoadenosine, 2-thiothymidine, 2-thiouridine, 5-bromocytidine, inosine, 6-azauridine, 6-chloropurine, 7-deazaadenosine, 7-deazaguanosine, 8-azaadenosine, 8-azidoadenosine, benzimidazole, N6-methyladenosine, pyrrolo-pyrimidine, 2-amino-6-chloropurine, 3-methyl adenosine, 5-propynylcytidine, 5-propynyluridine, 5-fluorouridine, 5-methylcytidine, 7-deazaadenosine, 7-deazaguanosine, 8-oxoadenosine, 8-oxoguanosine, O(6)-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate moieties (e.g., phosphorothioates or 5'-N-phosphoramidite linkages), and/or other naturally and non-naturally occurring bases substitutable into the polymer, including substituted and unsubstituted aromatic moieties. In some cases, the polynucleotide can include DNA, RNA, modified DNA, modified RNA, antisense oligonucleotides, expression plasmid systems, nucleotides, modified nucleotides, nucleosides, modified nucleosides, intact genes, or combinations thereof. Other examples of polynucleotides include interfering RNA, natural or unnatural siRNAs, shRNAs, microRNAs, ribozymes, DNA plasmids, antisense oligonucleotides, randomized oligonucleotides, or ribozymes. A nucleic acid sequence may be composed of DNA nucleotides, RNA nucleotides or a combination of both types and may include natural nucleotides, chemically modified nucleotides, and synthetic nucleotides.

"Amino acid sequence" is defined as a sequence composed of any one of the 20 naturally appearing amino acids, amino acids which have been chemically modified, or composed of synthetic amino acids. The terms "protein" and "peptide" refer to compounds comprising amino acids joined via peptide bonds and are used interchangeably. As used herein, where "amino acid sequence" is recited herein to refer to an amino acid sequence of a protein molecule. An "amino acid sequence" can be deduced from the nucleic acid sequence encoding the protein.

Sequence "identity" refers to the number of matching residues (expressed as a percentage) in a sequence alignment between two sequences of the alignment. As used herein, percentage identity of an alignment is calculated using the number of identical positions divided by the greater of the shortest sequence or the number of equivalent positions excluding overhangs wherein internal gaps are counted as an equivalent position. For example, the polypeptides GGGGGG (SEQ ID NO: 26) and GGGGT (SEQ ID NO: 32) have a sequence identity of 4 out of 5 or 80%. For example, the polypeptides GGGPPP (SEQ ID NO: 33) and GGGAPPP (SEQ ID NO: 34) have a sequence identity of 6 out of 7 or 85%.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted, or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Some proteins are recovered using denaturants and protein-refolding procedures. Common expression systems, for the expression of a protein coded for by foreign DNA carried by the vector and introduced to the host cell include E. coli host cells and plasmid vectors, insect host cells and baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective, rat YB2/3HL.P2.G11.16Ag.20 cell (ATCC CRL1662, hereinafter referred to as "YB2/0 cell"), and the like.

In vitro (cell-free) protein expression systems typically use translation-compatible extracts of whole cells or compositions that contain components sufficient for transcription, translation, and optionally post-translational modifications such as RNA polymerase, regulatory protein factors, transcription factors, ribosomes, tRNA cofactors, amino acids, and nucleotides. In the presence of an expression vectors, these extracts and components can synthesize proteins of interest. Cell-free systems typically do not contain proteases and enable labeling of the protein with modified amino acids. Some cell free systems incorporate encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

In certain embodiments, this disclosure relates to recombinant peptides comprising sequences disclosed herein or variants or fusions thereof wherein the amino terminal end or the carbon terminal end of the amino acid sequence are optionally attached to a heterologous amino acid sequence, label, or reporter molecule. In certain embodiments, this disclosure relates to recombinant peptides comprising sequences disclosed herein or variants or fusions thereof wherein the selected amino acid sequences that are critical for the high affinity binding to a target molecule are optionally attached to a heterologous amino acid sequence, label, or reporter molecule.

The term "fusion" when used in reference to a polypeptide refers to a chimeric protein containing a protein of interest joined to an exogenous protein fragment (the fusion partner). The fusion partner may serve various functions including enhancement of solubility of the polypeptide of interest, providing new function of the peptide, as well as providing an "affinity tag" to allow purification of the recombinant fusion polypeptide from a host cell or from a supernatant or from both. If desired, the fusion partner may be removed from the protein of interest after or during purification.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. A label includes the incorporation of a radiolabeled amino acid, a fluorescent dye, or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$) fluorescent labels (such as fluorescein isothiocyanate (FITC), rhodamine, lanthanide phosphors, or near infrared dyes), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, this disclosure relates to the recombinant vectors comprising a nucleic acid encoding a peptide disclosed herein or fusion protein thereof and optionally a selectable marker. A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme, which confers a blue color in the presence of X-gal (5-bromo-4-chloro-3-indolyl-β-D-galactoside). If a recombinant insertion inactivates the lac-z-gene, then the resulting colonies are colorless. There may be one or more selectable markers, e.g., an enzyme that can complement the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: amp$^r$, cam$^r$, tet$^r$, blasticidin$^r$, neo$^r$, hyg$^r$, abx$^r$, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferase1 (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

"Radiation therapy" is defined as a cancer treatment that uses high-energy x-rays or other types of radiation to kill cancer cells or keep them from growing. There are two types of radiation therapy. External radiation therapy, which uses a machine outside the body to send radiation to the cancer. Internal radiation therapy uses a radioactive substance sealed in needles, seeds, wires, or catheters that are placed directly into or near the cancer. The way the radiation therapy is administered is directly dependent on the type and stage of the cancer.

"Chemoradiation therapy" is defined as a therapy that combines chemotherapy and radiation therapy to increase the effects of both.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others. The cancer to be treated in the context of the present disclosure may be any type of cancer or tumor.

Targeted Delivery of Theranostic Nanoparticles Carrying Immune Modulators for Activation of Tumor-Specific Immune Responses Due to their small size (3-10 nm), iron oxide nanoparticles (IONPs) are able to utilize the enhanced permeability and retention (EPR) effect to extravasate through the abnormal, "leaky" tumor vasculature and actively target PD-L1 overexpressing cells in tumor cells and tumor microenvironment in comparison to conventional antibody-based therapies that are delivered all over the body in normal organs and tissues. One of the major challenges in immunotherapy is that tumor antigens are poorly immunogenic, and many immunogenic mutant proteins localize inside tumor cells. The combined treatment using tumor cell-targeted nanoparticle drug carriers with PD-L1 targeted nanoparticles has the potential to destroy tumor cells, expose intracellular, immunogenic tumor antigens, promote the up-take of macrophages, and process antigens for presentation to T and B cells. Meanwhile, inhibition of PD-L1 mediated immune suppression function by the PD-L1 blocking peptide conjugated nanoparticles should enhance overall tumor-specific T cell responses. Conventional anti-PD1 or PD-L1 antibody-mediated immunotherapies lack the ability to enhance presentation of immunogenic intracellular mutant proteins. The short PD-L1 blocking peptides reported herein have dual functions of tumor targeting and blocking PD-L1 that is highly expressed by many tumor cells as well as tumor stromal fibroblasts and macrophages. Furthermore, about 20 to 30 peptides could be conjugated on the surface of one nanoparticle, which should enhance the efficiency of PD-1/PD-L1 inhibition, whereas an anti-PD-L1 antibody can only block one PD-L1 molecule. An advantage of delivering PD-L1 blocking agents, such as antibodies or peptides, using nanoparticles is the limited bio-distribution in vivo that should only include the tumor microenvironment and macrophages or the RES system in the liver and spleen. However, conventional PD-1 or PD-L1 antibody therapies often have systemic effects and leads to dysregulation of the immune system and possible autoimmune diseases.

One of the major challenges in immunotherapy is that human cancers are enriched in tumor stroma, and the stroma barrier prevents efficient intratumoral delivery and distribution of PD-L1 or PD1 antibodies. For example, results of recent clinical trials using antibody therapy to block PD-L1 and PD-1 did not show significant therapeutic response in pancreatic cancer patients. The poor responses in pancreatic cancer are thought to be due to extensive tumor stroma. Tumor stroma consists of 50% to 80% of the tumor mass in pancreatic cancer tissue creating a physical barrier to block antibody delivery and infiltration of T cells into tumor tissues. Receptor targeted nanoparticle drug carriers disclosed herein have the potential to improve the therapeutic response of immunotherapy through the following mechanisms: 1) delivering of a high level of targeted nanoparticles into tumors promoting massive infiltration of immune cells, including T cells and antigen presenting cells (into tumor center areas to create pro-immune environment to facilitate the activation of immune responses); 2) destroying tumor cells to release tumor specific antigens; 3) breaking tumor stromal barriers by theranostic nanoparticles that increase T cell infiltration into deep tumor tissues; and 4) targeting delivery of PD-1 like peptide conjugated nanoparticles into tumor that blocks PD-L1 on tumor cells and stromal fibroblasts and macrophages (to activate tumor specific T cell responses and to enhance the effect of cytotoxic T cells).

In order to minimize adverse side effects as well as to enhance intratumoral delivery and tumor-specific immune responses, IONPs were developed carrying peptide-based antagonists to PD-L1. It is contemplated that these nanoparticles can be used as monotherapy and as a combination therapy with targeted theranostic nanoparticles carrying chemotherapeutic drugs.

Preliminary studies used i.p. delivery of unconjugated anti-mouse PD1 antibody in combination with uPAR targeted nanoparticles carrying a chemotherapy drug, cisplatin. This was done to demonstrate the feasibility of blocking the PD-1/PD-L1 interaction for enhancing anti-tumor growth effects. A receptor targeted nanoparticle carrying a chemotherapy drug, cisplatin (Cys), was used in a mouse pancreatic cancer model. However, an antibody has a relatively large size of 2×8 nm, which is too large for conjugation to the magnetic iron oxide nanoparticle optimized for intratumoral delivery (a core size of 5 nm). Therefore, two PD1-like peptides were designed by selecting the key PD-L1 binding domains of PD1 amino sequences and fusing them into a short peptide ligand with 35 (PD1-Y) or 37 (PD1-Lin, Linear) amino acids. These PD1-like peptides have several necessary amino acid modifications to retain domain structures, a short his tag (4) for conjugation and a cysteine (Cys), for labeling fluorescence dye molecules. In one, a short his tag (4×) was strategically placed in the middle of the PD-1 like peptide (PD1-Y) to create a 3-D structure for PD-L1 binding. In another, designated PD-1(Lin), the peptide is linear. In PD-L1 (Lin) binding domains are fused together with a his tag at the carboxyl-terminal. Each peptide contains a poly-histidine tag for conjugation to nitrilotriacetic acid-copper (NTA-Cu) functionalized IONPs to ensure the correct orientation of the PD1 binding domains.

Nanoparticles

This disclosure relates to nanoparticles comprising peptide-based antagonist of PD-L1 as a targeting moiety. In certain embodiments, the targeting moiety is a peptide comprising SEQ ID NO: 1, 2, or 3 or variants thereof. When reference is made to a particle or nanoparticle comprising a peptide, it is understood that the peptide is bound to the particle through a polymer coating, either through covalent bonds or other binding interactions, e.g., hydrophobic or hydrophilic binding or chelating interactions. In certain embodiments, a particle or nanoparticle comprising a peptide is bound to the particle mediated by interaction of the short his-tag with NTA-Cu that is conjugated to a polymer coating of the particle.

Within certain embodiments, the compositions and methods disclosed herein may be utilized with a variety of polymer-coated particles such as, e.g., quantum dots (QDs), metal particles, gold, silver, iron, and iron-oxide nanoparticles (IONPs). IONPs are typically prepared with a mean particle diameter of 3-200 nm. IONPs may be prepared by aging a stoichiometric mixture of ferrous and ferric salts in aqueous media under basic conditions. Control over particle size (3-20 nm) and shape is provided by adjusting the pH, ionic strength, and the concentration of the growth solution. The nanoparticles can be functionalized in situ using additives such as organic compounds (e.g. sodium citric) or polymers (e.g. dextran, polyvinyl alcohol). Other metals such as gold, cobalt, nickel, and manganese may be incorporated into the material.

High-temperature decomposition of $Fe(CO)_5$ in organic solvents is another way to prepare IONPs. Size (3-19 nm) can be varied using alternative temperatures. Flame spray pyrolysis yields a range of magnetite, maghemite and wustite (FeO) particles IONPs. Iron precursor such as $Fe(CO)_5$ and $Fe(NO_3)_3$ may be used. Flame spray pyrolysis can be used to produce different nanoparticles ($TiO_2$, ZrO2, silica, etc.) as well as hybrid particles (e.g. silica-IONPs).

Hydroxyl groups on the IONP provide a place for synthetic attachment of different functional groups. A range of chemistries can be used to stabilize metal nanoparticles exploiting electrostatic, hydrophobic, chelating, and covalent interactions. Carboxylic acid groups can interact with the surface of IONPs by coordination processes. IONP synthesis in organic solvents is typically conducted in oleic acid. A polymer coating on the IONPs is preferred. Polymer attachment to the IONP surface maybe accomplished by using an initiator fixed to the surface of the IONPs. Thereafter, the polymer is grown from the surface. Alternatively, a functional, pre-formed polymer is grafted onto IONPs in situ. Copolymers with hydrophobic groups, carboxylic acid groups, polyethylene glycols, or amine groups are contemplated. Polymers with a hydrophilic block and a hydrophobic block are contemplated. See Yang et al., Clin Cancer Res, 2009 15:4722; Lin et al., Small, 2008, 4(3):334-341; Yu et a., Nanotechnology, 2006, 17:4483-4487; Park et al., J. Mater. Chem., 2009, 19, 6412-6417; Boyer et al. NPG Asia Mater., 2010, 2(1):23-30, Kim et al., Nanotechnology, 2011, 22, 155101; all hereby incorporated by reference in their entirety.

Conjugating molecules or polypeptides to the polymers can be accomplished using a variety of methods. Typically, primary amine containing compounds and proteins may be conjugated to the carboxylic acid groups on the polymer mediated by a coupling reagent such as EDAC. See Yang et al., Small, 2009, 5(2):235-43, hereby incorporated by reference in its entirety. Other coupling methods are contemplated, e.g., poly-histidine sequence may be incorporated by recombinant methods into a polypeptide sequence of the targeting moiety. A poly-histidine chelating agent may be coupled to the polymer surface, e.g., NTA-Ni or NTA-Cu. Mixing the histidine tagged polypeptide sequence attaches it to the polymer surface linked through the chelating agent NTA. The avidin/streptavidin-biotin interactions may be used, e.g., biotin may be coupled to the polymer surface and streptavidin may be expressed as a chimera with the targeting moiety.

In addition to the peptides disclosed herein, the particles may comprise a second targeting moiety. In certain embodiments the targeting moiety is an amino-terminal fragment (ATF) of uPA, e.g., amino terminal fragment (ATF, 135 aa) of human uPA (17 kDa) (SEQ ID NO: 5) SNELHQVPSNCDCLNGGTCVSNKYFSNIHWCNCP-KKFGGQHCEIDKSKTCYEGNGHFY RGKASTDTM-GRPCLPWNSATVLQQTYHAHRSDALQLGLGKH-NYCRNPDNRRRPWCY VQVGLKPLVQECMVHDCA-DGK or (ATF, 68 aa) of human uPA (SEQ ID NO: 6) SNELHQVPSNCDCLNGGTCVSNKYFSNIHWCNC-PKKFGGQHCEIDKSKTCYEGNGHFY RGKASTDTMG, or human ATF-MMP14 (SEQ ID NO: 7) MSNEL-HQVPSNCDCLNGGTCVSNKYFSNIHWCNCPKK- FG-GQHCEIDKSKTCYEGNGHF YRGKASTDGAPIQGL-KWQHNEITFCIQNYTPKVGEYATYEAIRKAFRVWE-SATPLRFRE VPYAYIREGHEKQADEVIIFFAEGFHGD-STPFDGEGGFLAHAYFPGPNIGGDTHFDSAEPW TVRNEDLNGNDIFLVAVHELGHALGLEHSSDPSAIM-

APFYQWMDTENFVLPDDDRRGI QQLYGGESGFPTKMPPQPRTTSRPSVPDKPKNPTYGPNIEIHHHHH).

ATF or ATF-MMP14 may be produced from an *E. coli* BL21 bacterial expression system using a pET20a plasmid (Invitrogen, Grand Island, NY) containing the ATF or ATF-MMP14 cDNA sequence. Urokinase plasminogen activator (uPA) is a serine protease that regulates multiple pathways involved in matrix degradation, cell motility, metastasis, and angiogenesis. Interaction of the N-terminal growth factor domain of uPA with its cellular receptor (uPAR) results in the conversion of the plasminogen to a serine protease, which is a central regulator of the activation of other proteases including the matrix metalloproteinases (MMPs). Studies have shown that the uPA/uPAR complex controls the motility of both tumor and endothelial cells. In addition to its role in activation of the process for degradation of extracellular matrix, uPAR also activates α5β1 integrin and ERK signaling through interaction with EGFR and induces cell proliferation. Additionally, the uPA/uPAR complex can bind to the matrix protein, vitronectin, in association with transmembrane integrins, and activate intracellular signaling molecules such as protein kinases promoting cell adhesion, proliferation, and migration.

The uPAR-binding domain of uPA is located to the amino-terminal fragment (ATF) of uPA. Studies have shown that ATF is a potent uPA binding antagonist to its high affinity receptor (uPAR) at the surface of both tumor and endothelial cells. Systemic or local delivery of a non-catalytic amino-terminal fragment (ATF) of uPA (residues 1-135) using an adenoviral vector or conjugated peptides prevents the formation of the uPA/uPAR complex, thus inhibiting tumor growth and angiogenesis. Yang et al., Clin Cancer Res., 2009, 15(14):4722-32, hereby incorporated by reference in its entirety, discuss the preparation of targeted iron oxide nanoparticle using a recombinant peptide containing the amino-terminal fragment of urokinase-type plasminogen activator (uPA) conjugated to magnetic iron oxide nanoparticles, referred to as amino-terminal fragment conjugated-iron oxide nanoparticle (ATF-IONP). This nanoparticle targets uPA receptor which is overexpressed in breast cancer tissues.

In certain embodiments, the second targeting moiety is a moiety that binds EGFR or HER-2. The human epidermal growth factor receptor (EGFR) family includes EGFR (HER-1), EGFR-2 (HER-2), EGFR-3 (Her-3) and EGFR 4 (HER-4). The ligands that bind to EGFRs are divided into EGFR-like ligands such as EGF and TGF-α, and the heregulins. These ligands bind to EGFR monomers to promoter receptor dimerization and oligomerization that ultimately results in the activation of the EGFR signaling pathway. This EGFR signaling pathway plays a role in the regulation of cell proliferation, survival, and differentiation.

Human breast carcinomas with a triple negative subtype express high levels of the EGF receptors. Her-2 positive subtype breast cancer expresses a high level of Her-2 receptor. Overexpression of those receptors have been associated with highly aggressive breast cancer types and a poor response to therapeutic agents. Prior preclinical and clinical studies have shown that blocking the EGFR or HER-2 via monoclonal antibodies or inhibition of EGFR tyrosine kinase with small molecule inhibitors inhibits the growth of breast cancers and sensitize chemotherapy responses. Single-chain antibodies to EGFR that contain the specific EGFR binding region but lack the Fc region have been isolated from human scFv phage display libraries. Yang et al., Small, 2009, 5(2):235-43, hereby incorporated by reference in its entirety, discuss the preparation of EGFR targeted nanoparticles conjugating a single-chain anti-EGFR antibody (ScFvEGFR). A high affinity Her-2 binding affibody conjugated magnetic iron oxide nanoparticle has been shown to target to Her-2 expressing human ovarian tumors allowing for non-invasive tumor imaging in an orthotopic human ovarian cancer model in nude mice. (Satpathy M, & Yang L et al. Small, 2014; 10(3):544-55).

Iron oxide nanoparticles conjugated to a purified antibody that selectively binds to the epidermal growth factor receptor (EGFR) deletion mutant (EGFRvIII) present on human glioblastoma multiforme (GBM) cells were used for therapeutic targeting and MRI contrast enhancement of experimental glioblastoma, both in vitro and in vivo, after convection-enhanced delivery (CED). See Hadjipanayis et al., Cancer Res, 2010, 70:6303, hereby incorporated by reference in its entirety. In certain embodiments, this disclosure relates to a targeting moiety that is an antibody or antibody mimetic to EGFR or EGFRvIII for use in treating glioblastoma multiforme.

In certain embodiments, the second targeting moiety is a monoclonal antibody-610 that targets a surface antigen for use in treating colon carcinoma. See Cerdan et al., Magn Reson Med, 1989, 12:151-63 1989, hereby incorporated by reference in its entirety.

In certain embodiments, the second targeting moiety is an antibody to carcinoembryonic antigen (CEA) that targets CEA for use in treating colon tumors. See Tiefenauer et al., Magn Reson Imaging, 1996, 14:391-402, hereby incorporated by reference in its entirety.

In certain embodiments, the second targeting moiety is a monoclonal antibody L6 that targets a surface antigen for use in treating intracranial tumors. See Remsen et al., Am J Neuroradiol, 1996, 17:411-18, hereby incorporated by reference in its entirety.

In certain embodiments, the second targeting moiety is transferrin that targets transferrin receptor for use in treating carcinoma. See Kresse et al., Magn Reson Med, 1998, 40:236-42, hereby incorporated by reference in its entirety.

In certain embodiments, the second targeting moiety is a monoclonal antibody to Her-2, e.g., Herceptin, which targets Her-2 receptors for use in treating breast cancer. See Lee et al., Nat Med, 2007, 13:95-9; Artemov et al., Magn Reson Med, 2003, 49:403-8; and Huh et al., J Am Chem Soc, 2005, 127:12387-91, all hereby incorporated by reference in their entirety.

In certain embodiments, the second targeting moiety is the EPPT peptide that targets underglycosylated mucin-1 antigen (uMUC-1) for use in treating breast, colon, pancreas, and lung cancers. See Moore et al., Cancer Res, 2004, 64:1821-7, hereby incorporated by reference in its entirety.

In certain embodiments, the second targeting moiety is folic acid that targets folate receptor for use in treating mouth carcinoma and cervical cancers. See Chen et al., PDA J Pharm Sci Technol, 2007, 61:303-13; Sun et al., Small, 2006, 4:372-9; and Sonvico et al., Bioconjug Chem, 2005, 16:1181-8, all hereby incorporated by reference in their entirety.

In certain embodiments, the second targeting moiety is methotrexate that targets folate receptor for use in treating cervical cancer. See Kohler et al., Langmuir, 2005, 21:8858-64, hereby incorporated by reference in its entirety.

In certain embodiments, the second targeting moiety is a monoclonal antibody A7 that targets colorectal tumor antigen for use in treating colorectal carcinoma. See Toma et al., Br J Cancer, 2005, 93:131-6, hereby incorporated by reference in its entirety.

In certain embodiments, the second targeting moiety is chlorotoxin peptide that targets membrane-bound matrix-metalloproteinase-2 (MMP-2) for use in treating glioma. See Veiseh et al., Nano Lett, 2005, 5:1003-8, hereby incorporated by reference in its entirety.

In certain embodiments, the second targeting moiety is F3 peptide that targets surface-localized tumor vasculature for use in treating glioma. See Reddy et al., Clin Cancer Res, 2006, 12:6677-86, hereby incorporated by reference in its entirety.

In certain embodiments, the second targeting moiety is iRGD or RGD4C that targets integrins for use in treating melanoma and epidermoid carcinoma. See Zhang et al., Cancer Res, 2007, 67:1555-62 and Uchida et al., J Am Chem Soc, 2006, 128:16626-33, both hereby incorporated by reference in their entirety.

In certain embodiments, the second targeting moiety is luteinizing hormone releasing hormone (LHRH) that targets LHRH receptor for use in treating breast cancer. See Leuschner et al., Breast Cancer Res Treat, 2006, 99:163-76, hereby incorporated by reference in its entirety.

In certain embodiments, the second targeting moiety is CREKA peptide that targets clotted plasma proteins for use in treating breast cancer. See Simberg et al., Proc Natl Acad Sci USA, 2007, 104:932-6, hereby incorporated by reference in its entirety.

In certain embodiments, the second targeting moiety is an antibody to prostate specific membrane antigen (PSMA) that targets PSMA for use in treating prostate cancer. See Serda et al., Mol Imaging, 2007, 6:277-88, hereby incorporated by reference in its entirety.

lial, and stromal cells in many types of human cancers. See Nielsen et al., Int. J. Cancer 2007, 120, 2086-2095; Blasi & Carmeliet, Nat. Rev. Mol. Cell Biol. 2002, 3, 932-943; Pyke et al., Cancer Res, 1993, 53, 1911-1915.

In certain embodiments, this disclosure relates to particles comprising a core coated with a polymer, wherein the polymer is conjugated to a targeting moiety, a lysosomally degradable moiety, and a therapeutic agent such as gemcitabine, doxorubicin, cytosine arabinoside, mitomycin, or any therapeutic agent with an amine side group. In certain embodiments, the therapeutic agent is cisplatin. In certain embodiments, the particle is a metal nanoparticle or metal oxide nanoparticle, such as an iron oxide nanoparticle or elemental iron core nanoparticle with an oxide coat, or a quantum dot, e.g., those with a diameter of between about 5 to 200 nm or 10 to 100 nm. In certain embodiments, the lysosomally degradable moiety is the polypeptide GFLG (SEQ ID NO: 4) linked to the therapeutic agent. In certain embodiments, this disclosure relates to compositions comprising a polymer conjugated to a targeting moiety, lysosomally degradable moiety, and a therapeutic agent which are described herein. In one example, the lysosomally degradable moiety linked to the therapeutic agent is of the formula:

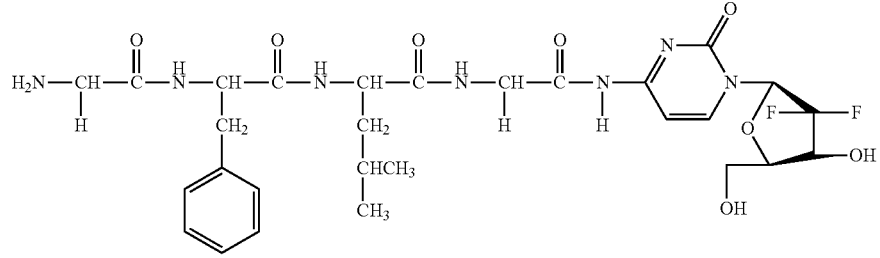

In certain embodiments, this disclosure relates to multifunctional nanoparticles comprising a targeting peptide disclosed herein, a nanoparticle, and a cargo. The nanoparticles can be either Quantum Dots (QDs) or gold nanoparticles that can be imaged optically or iron oxide nanoparticles (IONPs) that can be imaged via MM. In certain embodiments, the cargo is either a DNA cassette coding for a siRNA against an oncogene or survival factor, a chemotherapy drug or both.

Since siRNA is expressed from an RNA polymerase III (e.g., U6 or H1) promoter, a short hairpin siRNA (shRNA) gene may be cloned into expression vectors containing a polymerase III promoter to produce shRNAs from plasmids or viral vectors following transfecting into cells. See Brummelkamp et al., Science, 2002, 296, 550-553; Miyagishi & Taira, Nat. Biotechnol, 2002, 20, 497-500; McAnuff et al, J. Pharm. Sci. 2007, 96, 2922-2930; Bot et al., Blood, 2005, 106, 1147-1153. The shRNAs are further processed into siRNAs by a cellular endoribonuclease. DNA cassettes expressing shRNA containing a U6 promoter and a shRNA gene can be synthesized by a two-step PCR amplification protocol. See Castanotto et al., RNA, 2002, 8, 1454-1460 and Gou et al., FEBS Lett., 2003, 548, 113-118.

In certain embodiments provided herein is a particle that contains a polymer-coated nanoparticle core, e.g., a fluorescent quantum dot (QD) or MM contrast enhancing magnetic iron oxide nanoparticle (IONP), conjugated with about 10 to 20 DNA nanocassettes that contain a U6 promoter and a shRNA gene for in vivo siRNA gene expression following intracellular delivery. The nanoparticle is conjugated to a targeting peptide disclosed herein typically the amino terminal fragment (ATF) of the urokinase plasminogen activator (uPA), which targets its cellular receptor, uPAR. This receptor is highly expressed in tumors, angiogenic endotheor salts or derivatives thereof optionally substituted with one or more substituents. In certain embodiments, the polymer is an amphiphilic polymer comprising a hydrophobic section further comprising a hydrophobic chemotherapeutic agent.

In certain embodiments, the particle further comprises a fluorescent dye, e.g., a (3,3-dimethyl-indol-1-ium-1-yl)-N-alkylsulfonate dye or salt thereof such as one of the formula:

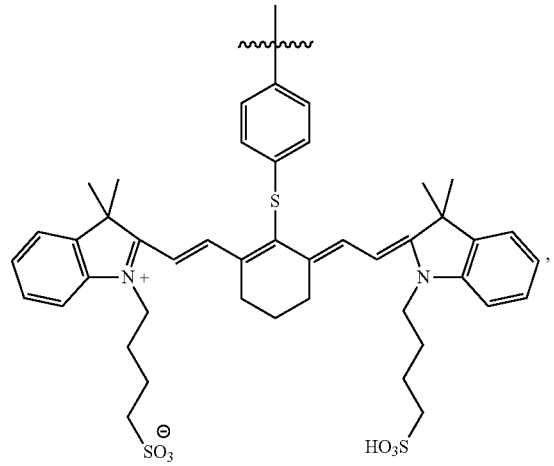

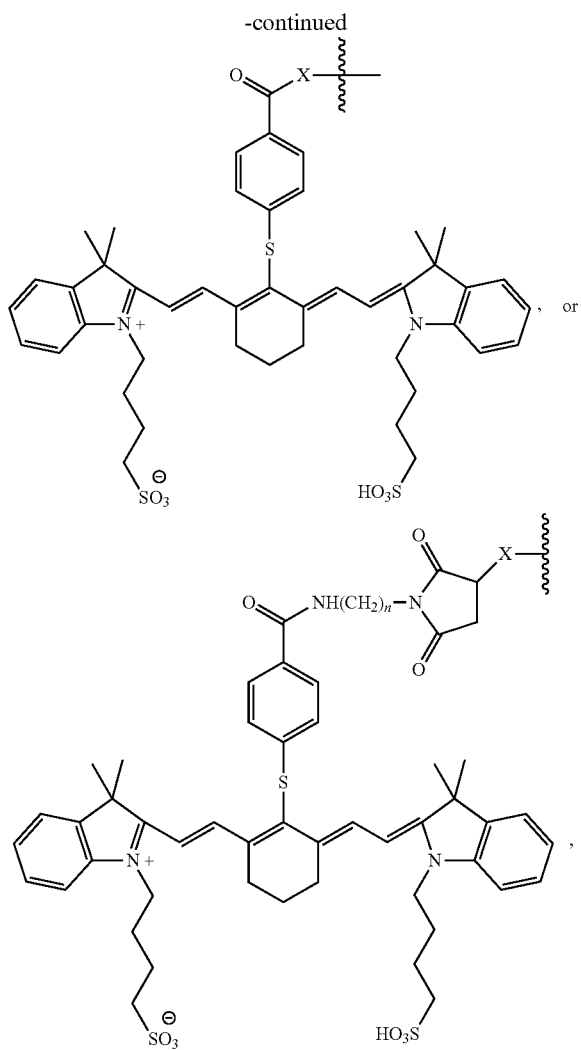

or salts or derivatives thereof optionally substituted with one or more substituents wherein X is S or NH and n is 2 to 22 or n is 4 to 22. In certain embodiments, the dye is conjugated to the free thiol group on cysteine or free amino group of the peptides or proteins.

Methods of Use

In certain embodiments, this disclosure relates to a method of treating cancer comprising administering an effective amount of a nanoparticle comprising a peptide disclosed herein or a peptide disclosed herein, to a subject in need thereof.

In certain embodiments, this disclosure relates to a method of treating cancer comprising administering an effective amount of a nanoparticle comprising a peptide comprising SEQ ID NO: 1, 2, 3, or variants to a subject in need thereof.

In certain embodiments, this disclosure relates to a method of treating cancer comprising administering an effective amount of a peptide comprising SEQ ID NO: 1, 2, 3, or variants to a subject in need thereof. In certain embodiments, the peptide may be administered in combination with a nanoparticle comprising an amino-terminal fragment (ATF) of uPA, ATF-MMP14, or the other peptide targeting ligands that may be incorporated into the nanoparticle.

In certain embodiments, this disclosure contemplates a combination chemotherapy comprising the administration of a first agent in combination with a second agent, wherein the first agent is a nanoparticle comprising a peptide having SEQ ID NO: 1, 2, 3, or variant thereof, wherein the second agent is an anti-CTLA-4 antibody such as Ipilimumab, or anti-PD-1 antibody such as nivolumab or pembrolizumab.

In certain embodiments, this disclosure contemplates a combination chemotherapy comprising the administration of a first agent in combination with a second agent, wherein the first agent is a nanoparticle comprising a peptide having SEQ ID NO: 1, 2, 3, or variant thereof, wherein the second agent is a nanoparticle comprising an amino-terminal fragment (ATF) of uPA or ATF-MMP14 and a chemotherapy agent attached to the nanoparticle or the chemotherapy agent is encapsulated by a polymer around the core of the particle.

In certain embodiments, this disclosure contemplates a combination chemotherapy comprising the administration of a first agent in combination with a second agent, wherein the first agent is a nanoparticle comprising a peptide having SEQ ID NO: 1, 2, 3, or variant thereof and an amino-terminal fragment (ATF) of uPA or ATF-MMP14 and optionally a chemotherapy agent attached to the nanoparticle or the chemotherapy agent is encapsulated by a polymer around the core of the particle; and the second agent is an anti-CTLA-4 antibody such as Ipilimumab, or anti-PD-1 antibody such as nivolumab or pembrolizumab.

In certain embodiments, the cancer is mediated by PD-L1. In certain embodiments, the cancer overexpresses a receptor of the targeting molecule in tumor cells, tumor endothelial cells, or tumor stromal fibroblasts compared to noncancerous tissue of an organ containing the cancerous tumor. In certain embodiments, the targeting molecule is an antibody or fragment, antibody mimetic, inhibitor, or aptamer targeting a protein or glycoprotein expressed on the surface of a cancerous cell. In certain embodiments, the cancer overexpresses uPAR, EGFR, or HER-2. In certain embodiments, the cancer is selected from pancreatic cancer, breast cancer, prostate cancer, lung cancer, skin cancer, bladder cancer, brain cancer, colon cancer, rectal cancer, kidney cancer, endometrial cancer, and thyroid cancer.

In certain embodiments, the cancer is selected from carcinoma, lymphoma, blastoma, sarcoma, and leukemia, non-small cell lung, squamous cell, small-cell lung, peritoneum, hepatocellular, gastrointestinal, pancreatic, glioma, cervical, ovarian, liver, bladder, hepatoma, breast, colon, colorectal, endometrial or uterine, salivary gland, kidney, liver, prostate, vulval, thyroid, hepatic, leukemia and other lymphoproliferative disorders, and various types of head and neck. In certain embodiments, the cancer can be primary or metastatic tumors.

In further embodiments, this disclosure relates to methods of treating cancer further comprising administering a particle or peptide disclosed herein comprising a second chemotherapy agent or administering a second chemotherapy to the subject separate from any chemotherapy agent contained in or attached to the particle and/or the surrounding polymer. In certain embodiments, particles disclosed herein are administered in an effective amount to treat a subject diagnosed with cancer or a cancerous tumor. In certain embodiments, the particles disclosed herein are administered in combination with a second anti-cancer agent such as, but not limited to, bevacizumab, gefitinib, erlotinib, temozolomide, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, idoxifene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, and/or lenalidomide or combinations thereof.

In certain embodiments, the methods disclosed herein may be used in combination with radiation and chemoradiation therapy.

In certain embodiments, this disclosure relates to a method for cancer diagnosis comprising administering an effective amount of a peptide disclosed herein or nanoparticle disclosed herein to a subject in need thereof and detecting the particle about the area of a cancerous cell or tumor.

Also contemplated are malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genito-urinary apparatus and, more particularly, childhood acute lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukemia, chronic myeloid leukemia, cancer of the colon, cutaneous T-cell lymphoma, endocrine pancreatic islet cells carcinoma, endometrial cancer, ependymoma, epithelial cancer, cancer of the esophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, tricoleukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukemia, myeloid leukemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, phaeochromocytoma, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, idoxifene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as, cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF);

epirubicin, cisplatin, capecitabine (ECX); methotrexate, vincristine, doxorubicin, cisplatin (MVAC).

In certain embodiments, this disclosure relates to methods of optical and MM imaging the nanoparticle in tumors. 3D-MRI enables monitoring of intratumoral distribution of nanoparticles and tumor responses to therapeutics contained on or in the nanoparticles.

In certain embodiments, this disclosure relates to nanoparticles coated with amphiphilic polymers conjugated with molecules useful for targeting tumors, monitoring the location of the nanoparticles administered to a subject by MRI, and viewing the presence of the nanoparticles during optical image-guided surgery.

In certain embodiments, this disclosure relates to uses of particles disclosed herein as a theranostics. Theranostics are therapeutics with physical properties that allows one to image molecular accumulation of the vehicles in vivo. Yang et al., WO/2007/018647, disclose binding and internalization of tumor targeted-iron oxide particles using MRI. See also Yang et al., J. Biomed. Nanotechnol., 2008, 4, 439-449. Lammers et al., Biomaterials, 2009, 30(2):3466-3475, disclose the simultaneous delivery of doxorubicin and gemcitabine to tumors in vivo using polymeric drug carriers.

In certain embodiments, this disclosure relates to methods comprising preoperatively administering a composition comprising nanoparticles disclosed herein and monitoring the location of the particles in the subject by detecting the particles by MRI (magnetic resonance imaging) in an area of the subject. In certain embodiments, the method further comprises the steps of operating on the subject in the area of detected particles, imaging dye identified tumors binding the targeting molecule, and surgically removing dye identified tumors or tissue.

In certain embodiments, this disclosure relates to methods comprising preoperatively administering cancer targeted nanoparticles conjugated to dyes disclosed herein to a subject, optically imaging a tumor that bind the nanoparticles intra-operatively, and removing tumors targeted with the nanoparticles.

In certain embodiments, this disclosure contemplates imaging and effecting cancer cell lysis or other cell lysis with particles using iron or iron oxide cores. See WO2009/120702.

In certain embodiments, this disclosure relates to targeting cancer by local hyperthermia using composition and methods disclosed herein. Local hyperthermia can lead to induction of apoptosis, heat-shock protein release, and chemotherapy agent sensitivity of cancer cells by exposure of cancer cells containing particles with an iron or iron oxide core to an alternating magnetic field (<1000 kHz) that are safe to normal cells.

In certain embodiments, this disclosure relates to methods of lysing cancer cells comprising administering particles disclosed herein to a subject and adjusting magnetic fields proximate the subject to cause cell lysis of cancer cells that absorb the particles after administration. Typically, the magnetic field is an oscillating magnetic field, and the particles are heated to at least 37° C. in vivo typically greater than 41° C.

Pharmaceutical Compositions

In certain embodiments, this disclosure relates to pharmaceutical compositions comprising particles disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide. Optionally, the pharmaceutical composition further comprises a second anticancer agent.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the particles may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients such as lactose or milk sugar and polyethylene glycols, and the like.

Solid dosage forms such as tablets, capsules, pills, and granules can be prepared with coatings and shells, such as enteric coatings and others well known in the art. They may contain opacifying agents, and they can also be of such composition that they release the particles in a certain part of the intestinal tract in a delayed manner.

Liquid dosage forms for oral administration include pharmaceutically acceptable emulsions, solutions, suspensions, syrups, and elixirs. In addition to the particles, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols, and fatty acid esters of sorbitan or mixtures of these substances, and the like.

Besides such inert diluents, the composition can also include adjuvants, wetting agents, emulsifying and suspending agents, sweetening, flavoring, and perfuming agents. Suspensions, in addition to the particles, may contain suspending agents, as for example, ethoxylated iso-stearyl alcohols, polyoxyethylene sorbitol and sorbitan esters, microcrystalline cellulose, aluminum metal hydroxide, bentonite agar-agar, and tragacanth, or mixtures of these substances, and the like.

Pharmaceutical compositions typically comprise an effective amount of particles and a suitable pharmaceutical acceptable carrier. The preparations can be prepared in a manner known per se, which usually involves mixing the particles according to this disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

The pharmaceutical preparations of this disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the particles of this disclosure e.g., about 10, 25, 50, 100, 200, 300 or 400 mg per unit dosage.

The particles can be administered by a variety of routes including the oral, ocular, rectal, transdermal, subcutaneous, intravenous, intramuscular, or intranasal routes, depending mainly on the specific preparation used. The particles will generally be administered in an "effective amount," by which it is meant any amount of particles that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated.

Formulations containing particles described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, M D, 2000, and "Pharmaceutical dosage forms and drug delivery systems," 6th Edition, Ansel et al., (Media, PA: Williams and Wilkins, 1995). These references provide information on carriers, materials, equipment, and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, arginine, gums, or cross-linked polymers, such as cross-linked PVP (Polyplasdone XL™ from GAF Chemical Corp).

Stabilizers are used to inhibit or retard decomposition reactions which include, by way of example, oxidative reactions.

A "pharmaceutical composition" or "pharmaceutically acceptable" composition, is defined as a therapeutically effective amount of one or more of the compositions described herein, formulated together with one or more pharmaceutically acceptable carriers (additives) and/or diluents. As described in detail, the pharmaceutical compositions of the present disclosure can be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically-acceptable carrier" as used herein means a pharmaceutically-acceptable material, composition or vehicle, such as a liquid or solid filler, diluent, excipient, or solvent material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetra-acetic acid (EDTA), sorbitol, tartaric acid, phosphoric acid, and the like.

The compositions of the present disclosure can be given in dosages, generally, at the maximum amount while avoiding or minimizing any potentially detrimental side effects. The compositions can be administered in effective amounts, alone or in a cocktail with other compounds, for example, other compounds that can be used to treat a disease. An effective amount is generally an amount sufficient to inhibit the disease within the subject.

One of skill in the art can determine what an effective amount of the composition is by screening the composition using known methods. The effective amounts may depend, of course, on factors such as the severity of the condition being treated; individual patient parameters including age, physical condition, size, and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions of this disclosure can be varied so as to obtain an amount of the active ingredient that is effective to achieve the desired therapeutic response for a particular patient, composition, and mode of administration, without being toxic to the patient.

The selected dosage level may depend upon a variety of factors including the activity of the particular compound of the present disclosure employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of this disclosure employed in the pharmaceutical composition at levels lower than that required to achieve the desired therapeutic effect and then gradually increasing the dosage until the desired effect is achieved.

In some embodiments, a compound or pharmaceutical composition of this disclosure is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of this disclosure repeatedly over the life of the subject. For example, chronic treatments can involve regular administrations, for example one or more times a day, one or more times a week, or one or more times a month. In general, a suitable dose such as a daily dose of a compound of this disclosure will be that amount of the compound that is the lowest dose effective to produce a therapeutic effect. Such an effective dose will generally depend upon the factors described above.

EXAMPLES

Designed and Synthesized Two PD-L1 Blocking Peptides.

Although antibodies against PD-1 or PD-L1 have been used as immune checkpoint blocker for immunotherapy, due to their bulky size, conjugation of antibodies to the surface of the IONPs will significantly increase the size of the IONPs thus potentially inhibiting its efficient extravasation deep into tumor tissues. Additionally, only 2 to 3 antibodies can be conjugated to a single nanoparticle with a particle size of 20 nm.

To increase the efficiency of PD-L1 blocking in tumor tissues, it is important to increase the numbers of PD-L1 blocking ligands on nanoparticles. It was discovered that 20 to 50 short peptides (35 AA) could be conjugated to a single nanoparticle coated with polymer and NTA-cu. To select a peptide-blocking agent with a high affinity in PD-1 binding, two PD-L1 blocking peptides were designed and synthesized. Those peptides were derived from the PD-L1 binding domains of PD-1, which would bind to the PD-L1 expressed by tumor cells and stromal fibroblasts and macrophages and inhibit the binding of PD-1+ cells, namely T cells, and potentially rescue these cells from exhaustion and anergy, thus enhancing localized, cellular immune responses.

Asterisk marked amino acids are identified as "hot spots" of PD-1 for PD-L1 binding (FIG. 1A). PD-L1 blocking peptides were prepared (FIG. 1B). PD-1(Y): two PD-L1 binding domains of PD-1 separated by his-tag (4×) for highly affinity binding and PD-1(Lin): Two PD-L1 binding domains fused as a single peptide with his-tag at C-terminal.

Figure 5:
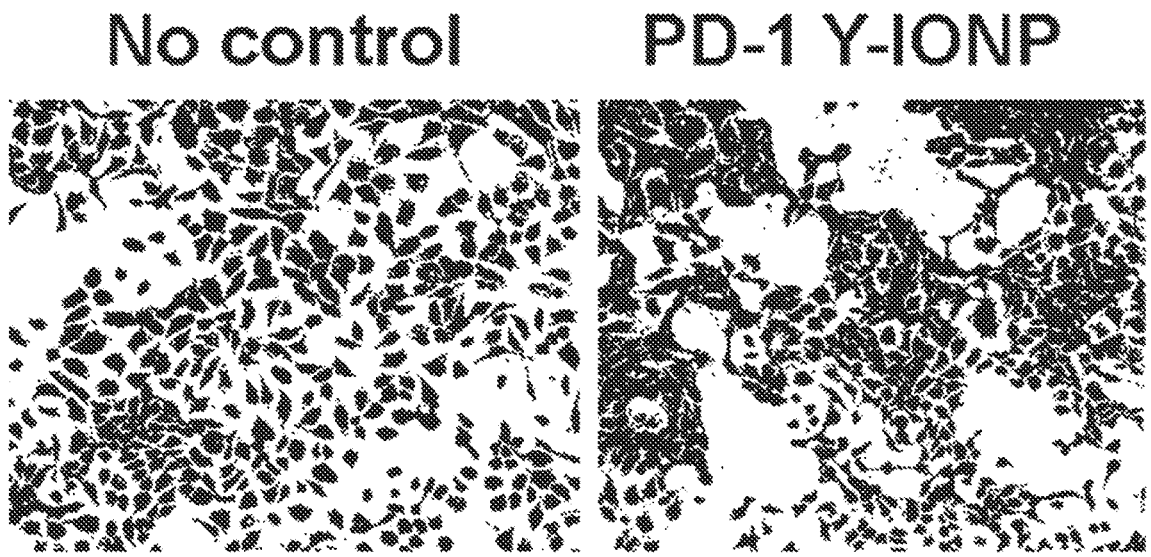
FIG. 5 shows Prussian blue staining of PD-1Y conjugated IONPs bound to primary cultures of human pancreatic cancer cells derived from a human pancreatic cancer patient tumor xenograft.
Figure 6:
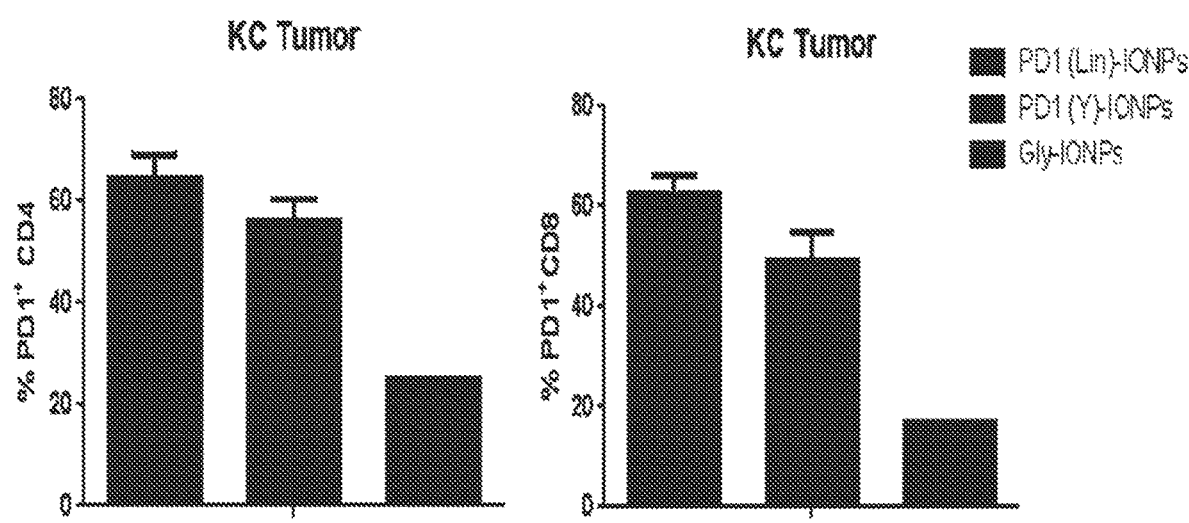
FIG. 6 shows data from flow cytometry analysis of CD4 and CD8 TIL cells isolated from s.c. pancreatic tumors following systemic deliveries of PD-1 Lin-IONP or PD-1 Y-IONP.

Since the binding affinity of the native PD-1 to PD-L1 is not very high (approximately 8.5 amino acid adjustments were made in the PD-1 peptide to improve binding. As shown in FIG. 1A, 5 of 17 amino acids in the first binding domain, and 4 of 14 amino acids in the second binding domain have been strategically replaced. For conjugation of such a short peptide to nanoparticles, it is important to ensure the correct orientation of the binding domains for high affinity binding. Four histidine residues are added between two binding domains (PD-1 Y), or at the end of the peptide (PD-1 (Lin)) for conjugating the peptides to the NTA-Cu on the surface of nanoparticles. Structural analysis of PD-1 Y and PD-1 (Lin) peptides revealed that the presence of his-tag in the middle of PD-1 Y peptide created a "Y" shaped peptide with two binding domains extended out for effective binding to PD-L1. However, PD-1 (Lin)

peptide has one binding domain exposed. The second binding domain is covered by the his-tag. Thus, conjugation of PD-1(Lin) through His-tag-NTA-cu may interfere with the binding of the second domain to PD-L1.

```
PD-1 (Y) - NWNRLSPSNQTEKQAAPHHHHCGAISLHPKAKIEE
(SEQ ID NO: 2, MW 4111.56)

PD-1(Lin) - NWNRLSPSNQTEKQAACGAISLHPKAKIEESPGHHHH
(SEQ ID NO: 3, MW: 3967.43)
```

Figure 4A:
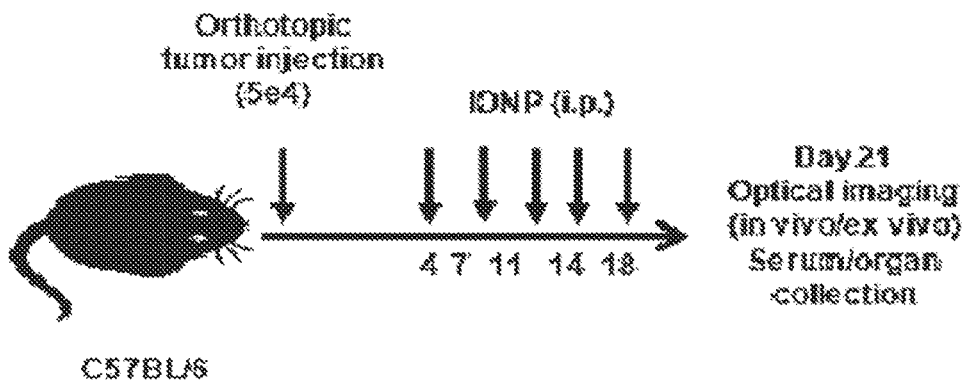
FIG. 4A illustrates a treatment protocol. A mouse Panc02 pancreatic cancer model was used.
Figure 4B:
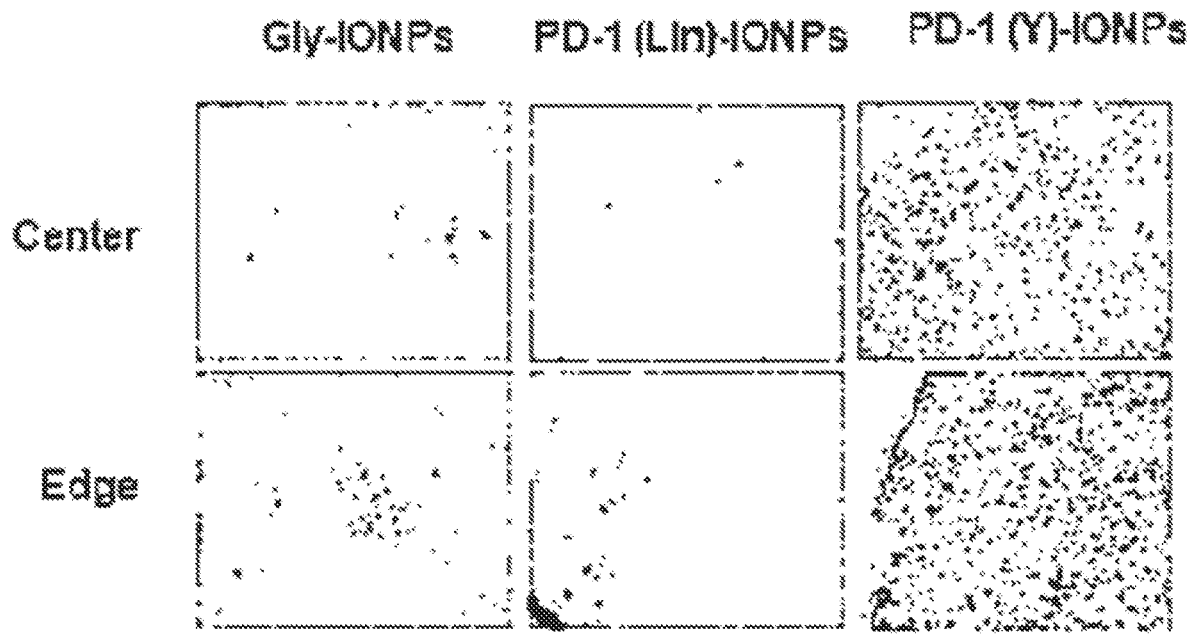
FIG. 4B shows Prussian blue staining of frozen tumor tissue sections. Dots show IONP positive cells.

Conjugation of His Tagged PD-1(Y) or PD-1 (Lin) Peptides to 5 nm Core Size and Polymer Coated IONPs that are Functionalized by NTA-Cu on the Surface of IONPs To determine the ability of PD-1 like peptides in binding to and blocking PD-L1, both peptides were conjugated to the nanoparticles mediated by a histidine (His) tag located either at the C-terminus (Lin) or in the middle of the sequence PD1 (Y). NTA-Cu is on the surface of IONPs (FIG. 2). PD-1 like peptides were mixed with NTA-Cu-IONP (core size 5 nm) at a molar ratio of peptide to IONP at 20:1 for 4 hours at room temperature. Unbound peptides were removed by 100K column spinning. If optical imaging was performed, PD-1 like peptides were labeled with maleimide NIR-830 dye. Ultra-small magnetic iron oxide nanoparticles (IONP) with a core size of 3.5 having an anti-fouling polymer coating were also produced.

Hyaluronic Acid Polymeric Nanoparticle (HANP) Using Cys-Thiol and Maleimide Mediated Conjugation Hyaluronic acid nanoparticles may be prepared by chemical conjugation of hydrophobic molecules. The outer hydrophilic shell prevents uptake by the reticuloendothelial system (RES). The hydrophobic moieties may be attached through the carboxylic acid group of hyaluronic acid (HA) using carbodiimide chemistry. Hyaluronic acid nanoparticles (HANP) were prepared by covalently conjugating hyaluronic acid with a hydrophobic moiety, 5β-cholanic acid. The resulting nanoparticle has hydrophilic surface and hydrophobic inside, where hydrophobic chemotherapy drugs can be encapsulated. After administrated in vivo, the enhanced permeability retention (EPR) effect and inherent CD44 targetability make HANP a dual tumor targeting drug carrier.

A urokinase-type plasminogen activator receptor and matrix metalloprotease 14 fusion protein, ATFmmp14, were conjugated onto surface of HANP/drug complex. HANP can be used to deliver therapeutic agents, such as SN38, camptothecin, paclitaxel and many other hydrophobic chemotherapy drugs as well as small molecule drugs. These protease-linked HANPs have the ability to break tumor stromal matrix and migrate inside tumor tissue to improve intratumoral nanoparticle distribution and potentially increase drug delivery into tumor cells.

The protease-linked and targeted HANP should have broad applications in targeted cancer therapy for many types of human cancers that have extensive tumor stromal components, such as pancreatic, triple negative breast, skin, head and neck, liver, sarcoma, and prostate cancers. The protease-linked and targeted HANP is capable of carrying different hydrophobic chemotherapy drugs for cancer-targeted therapy. Receptor targeted HANP for drug delivery into uPAR, EGFR, IGF-1R, or Her-2, positive tumor cells. A near infrared dye can be conjugated to the protease-linked targeting ligands, providing optical imaging capability. This stroma breaking polymeric drug delivery platform can be used for the treatment of non-oncology diseases with severe fibrotic and inflammatory tissues that prevent drug delivery into diseased cells or targets, such as chronic viral hepatitis, liver cirrhosis, fat liver, chronic tuberculosis, and atherosclerosis.

Hyaluronic acid polymeric nanoparticle (HANP) with a size of about 150 nm were designed using a unique cysteine in the loop region between two binding domains mediated by thiol side group (See SEQ ID NO: 2 and 3) and maleimide. These methods conjugate short peptides to the nanoparticle surface while retaining a good binding affinity. Furthermore, about 20 to 30 peptides can be conjugated to one nanoparticle. For near infrared optical imaging, NIR 830 dye can also be conjugated to the peptides or nanoparticles, resulting in two IONP based theranostic PD-L1 blocking nanoparticles with MRI and optical imaging ability, and one theranostic PD-L1 polymeric HANP with NIR optical imaging ability.

Specific Binding of PD-1 Like Peptides to PD-L1 Expressing Mouse Pancreatic Tumor Cell Lines Specific binding of PD-1 like peptides to PD-L1 has been demonstrated in vitro using three different assays. First, incubation of PD-1 Y or PD-1 Lin peptide conjugated IONPs with mouse pancreatic cancer cell lines, including Kras transgenic mouse pancreatic cancer derived KC and mouse pancreatic cancer Panc02 cells, led to the IONP binding tumors cells that were detected by Prussian blue staining. Cells incubated with control non-targeted poly-gly peptide conjugated IONPs had a very low level of IONPs.

Next, a competition-binding assay was performed to determine specificity of the PD-1 like peptides binding to PD-L1 on tumor cell surfaces. Fluorescent dye (FITC) labeled PD-1 Y or PD-1 Lin peptides (2 μg/ml) were mixed with different concentrations of an anti-mouse PD-L1 monoclonal antibody (BioX Cell™) that has been shown to block PD-L1. The peptides were then added to tissue culture plates with mouse pancreatic cancer KC cells. High levels of fluorescence intensity were observed on cells treated with both PD-1 Y and PD-1 Lin peptides (FIG. 3A). However, the binding of PD-1 Y to cells was reduced by addition of a high concentration (20 μg/ml) of the anti-PD-L1 antibody, suggesting that the PD-1 Y binding site on PD-L1 is the same as the PD-L1 antibody (FIG. 12).

A pull-down assay was conducted to confirm the binding of PD-1 like peptides specifically to PD-L1 protein on tumor cells. Cell lysates of mouse pancreatic cancer KPC cells derived from a Kras/p53 transgenic mouse pancreatic tumor were incubated with agarose beads coated with PD-1 like peptides through his-tag and NTA-Ni. Both PD-1 like peptides pulled down a high level of PD-L1 proteins, indicating specific binding of the PD-1 like peptides to PD-L1 (FIG. 3B).

PD-1 Like Peptides are Capable of Targeted Delivery of IONPs into Orthotopic Pancreatic Tumors Following Intraperitoneal (i.p.) or Systemic Delivery PD-L1 is upregulated in many tumor cells and tumor stromal cells. PD-1 like peptide-conjugated nanoparticles have the potential to serve as tumor targeted nanoparticles to be delivered into tumors for tumor imaging and immunotherapy. PD-1 like peptides can be used for targeted delivery of nanoparticles into tumors following systemic administration. Efficient delivery of PD-1 Y conjugated IONPs into pancreatic tumors has been tested in three mouse pancreatic tumor models and one human orthotopic pancreatic cancer patient tissue derived xenograft (PDX) model.

An orthotopic mouse PANCO2 pancreatic tumor model was established by injecting $5\times10^4$ of PANCO2 cells directly into the pancreas of the mice. Tumor bearing mice then received 5 treatments of i.p. delivery of NIR 830 dye labeled PD1-IONP conjugates and a non-targeting control that was conjugated with a poly-glycine peptide (Gly-IONPs) beginning on day 4 post tumor cell implantation once every 3 days (FIG. 4A). Mice were sacrificed and the abdominal cavity was opened to expose the location of the orthotopic pancreatic tumors. NIR optical imaging was performed to determine selective accumulation of the PD-1 like peptide-conjugated IONPs into pancreatic tumors. High levels of optical signals was detected in the orthotopic tumors, indicating targeted delivery into the tumors. Histological analysis of tumor tissues using Prussian blue staining revealed high levels of blue iron containing cells in the tumor obtained from the mice that received i.p. delivery of PD-1 (Y)-IONPs (FIG. 4B). Low to intermediate levels of IONP positive cells were seen in the tumors of the mice treated with non-targeted IONPs or PD-1(Lin)-IONPs (FIG. 4B). Taken together, PD-1 IONPs capable of binding to PD-L1 and expressing pancreatic tumor cells in vitro were developed. In vivo targeting to orthotopic PANCO2 tumors was demonstrated.

Effective targeted delivery of IONP by PD-1 like peptides into the orthotopic pancreatic tumors following i.p. delivery was also demonstrated in a mouse pancreatic KC tumor model that was established by intra-pancreatic injection of the UN-KC-6141 tumor cell line (KC) derived from the Pdx-1-Cre; LSL-K-rasG12D mice. One week following tumor cell injection, the mice received i.p. delivery of 800 pmol of NIR-830 dye labeled PD-1 Lin-IONP, PD-1 Y-IONP, or non-targeted Gly-IONP once every three days for three injections. Non-invasive whole body optical imaging was performed 48 hours following the last IONP injection and showed strong optical signals in the pancreatic tumor areas. A low level of the optical signal was found in the tumor area of the mice injected with non-targeted IONPs.

Following sacrificing mice, ex vivo optical imaging showed the strongest optical signal in the tumor obtained from the mice that received PD-1Y-IONP injection. NIR signal in the tumor obtained from the mice that received PD-1Lin-IONP was lower than that of the PD-1Y-IONP treated tumors and higher than that of non-targeted Gly-IONP treated tumors. Histological analysis of tumor tissues further confirmed the presence of a high level of IONP positive cells (blue stained cells) in the pancreatic tumors treated with PD-1Y-IONPs. A high level of NIR signal was also co-localized with the IONP positive tumor cell areas. Therefore, results from two different mouse pancreatic tumor models both showed that PD-1Y-IONPs have a higher efficiency in targeted delivery into pancreatic cancers compared to PD-1 Lin-IONPs.

Mouse PD-1 can bind to human PD-L1, and human PD-1 also binds to mouse PD-L1. With a translational goal, a mouse PD-1 peptide sequence was used to engineer the PD-1 like peptides so that the same reagent can be used for future clinical applications. The PD-1Y-IONP was able to bind to primary culture of human pancreatic cancer cells derived a human pancreatic cancer patient tissue-derived xenograft (PDX) in mice (FIG. 5). I.p. delivery of the NIR-830-dye-PD-1 Y-IONPs into the nude mice bearing the orthotopic human pancreatic PDX tumor xenografts showed the selective accumulation of the nanoparticles in the pancreatic tumors. Therefore, PD-1 Y-IONP has the potential for further development as a targeted immunotherapy agent for the applications in human cancer patients.

The effect of systemic delivery of PD-1 peptide conjugated IONPs on tumor growth and function of immune cells in tumors using a subcutaneous (s.c) tumor model derived from KC tumor cell line was examined. One of the studies used a mouse tumor model bearing two s.c. tumors on each side of the flank areas, derived from the mouse pancreatic tumor KC cell line and the UN-KPC-691 (KPC) cell line that was established from mouse pancreatic cancer from Pdx1-Cre/LSL-KRAS/p53 R175H transgenic mice.

Following three systemic deliveries of PD-1 Lin-IONP or PD-1 Y-IONP for 48 hours, strong NIR optical signals were detected in both KC and KPC tumors on the same mouse. KPC tumors grew slower than KC tumors in the wild type Kras transgenic mice. The mean signal intensity was lower. Consistent with results in orthotopic pancreatic tumor models using i.p. delivery of the PD-1-IONPs, intravenous delivery of the nanoparticles led to a higher level of the accumulation of PD-1 Y-IONP into s.c. KC or KPC tumors compared to that of PD-1 Lin-IONP treated tumors. Results of ex vivo imaging of normal organs also showed a very low signal in normal organs, including the liver, spleen, lung, and heart. Low to intermediate levels of optical signals were detected in some areas of intestine and kidney.

Forty-eight hours following the last of three systemic deliveries of PD-1 Y-IONP or non-targeted Gly-IONP (800 pmol/each dose) into the mice bearing s.c. KC tumors, T2-weighted MRI was performed on the mice. In comparison with the MM contrast in tumors before and after the nanoparticle injections, marked decreases in MRI T2 signal were found in the tumors treated with PD-1 Y-IONPs. Results of this study also suggested that on can use NIR-830-dye-PD-1Y-IONP as an imaging probe for non-invasive detection of PD-1L expression in human tumors as a therapeutic indication for PD-1/PD-L1 targeted immunotherapy.

Figure 8:
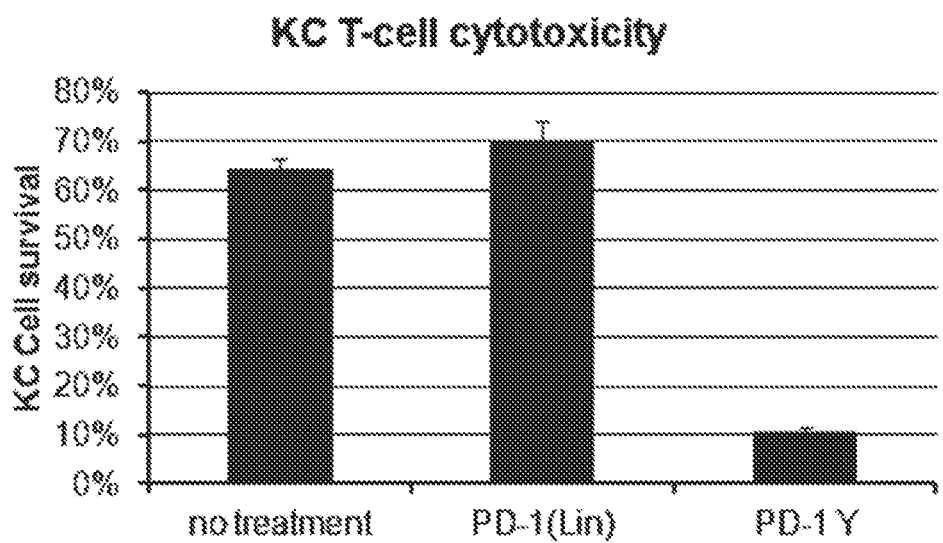
FIG. 8 shows data on the evaluation of pancreatic cancer specific T cell cyto-toxicity in the KC mouse pancreatic cancer model. Mice bearing orthotropic KC tumors received three i.p. deliveries of PD-1 Lin-IONP or PD-1 Y-IONP once every 3 days. CD3+ T cells were isolated from splenocytes and co-cultured with the KC cells for 72 hours. AlarmaBlue™ cell proliferation assay was used to determine the percentage of viable cells in each group. O.D. value from the KC cell culture without the addition of CD3+ T cells were designated as 100%.

Targeted Delivery of PD-1 Lin and PD-1 Y-IONP into Pancreatic Tumors Increase Both CD4 and CD8 TIL Cell Population To evaluate the effect of targeted delivery of PD-1 peptide conjugated IONPs on tumor growth and changes in immune cell population and function, TIL cells were examined in the KC pancreatic tumor model. Following three i.v. deliveries of PD-1Lin-IONP or PD-1Y-IONP into mice bearing s.c. tumors, tumors were collected and TIL cells were isolated. Cells were labeled with CD4 and PD-1 antibodies or CD8 and PD-1 antibodies, and then analyzed by flow cytometry. Targeted delivery of PD-1 Lin and PD-1 Y-IONP into pancreatic tumors increase both CD4 and CD8 TIL cell population (FIG. 8). Nanoparticle-induced infiltration of TIL cells into tumor tissues should create a pro-immune environment for activation of tumor specific cytotoxic T cell responses. Although the level of PD-1 Lin-IONP in tumors was found to be lower than when using PD-1Y-IONP, similar levels of TIL cells were detected in both groups. In another orthotopic KC tumor model, three i.p. deliveries of PD-1Y-IONPs led to increased levels of CD8 TIL cells in both tumor edge and tumor central areas.

Figure 7A:
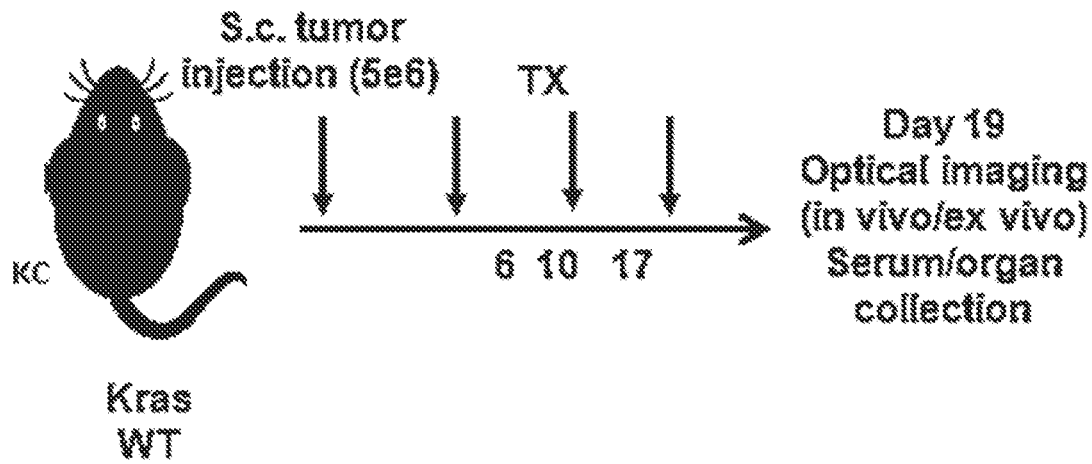
FIG. 7A illustrates a treatment protocol. Three i.v. injections of 100 μg/injection of anti-PD-L1 antibody or equivalent amount of PD-1Y-IONP.
Figure 7B:
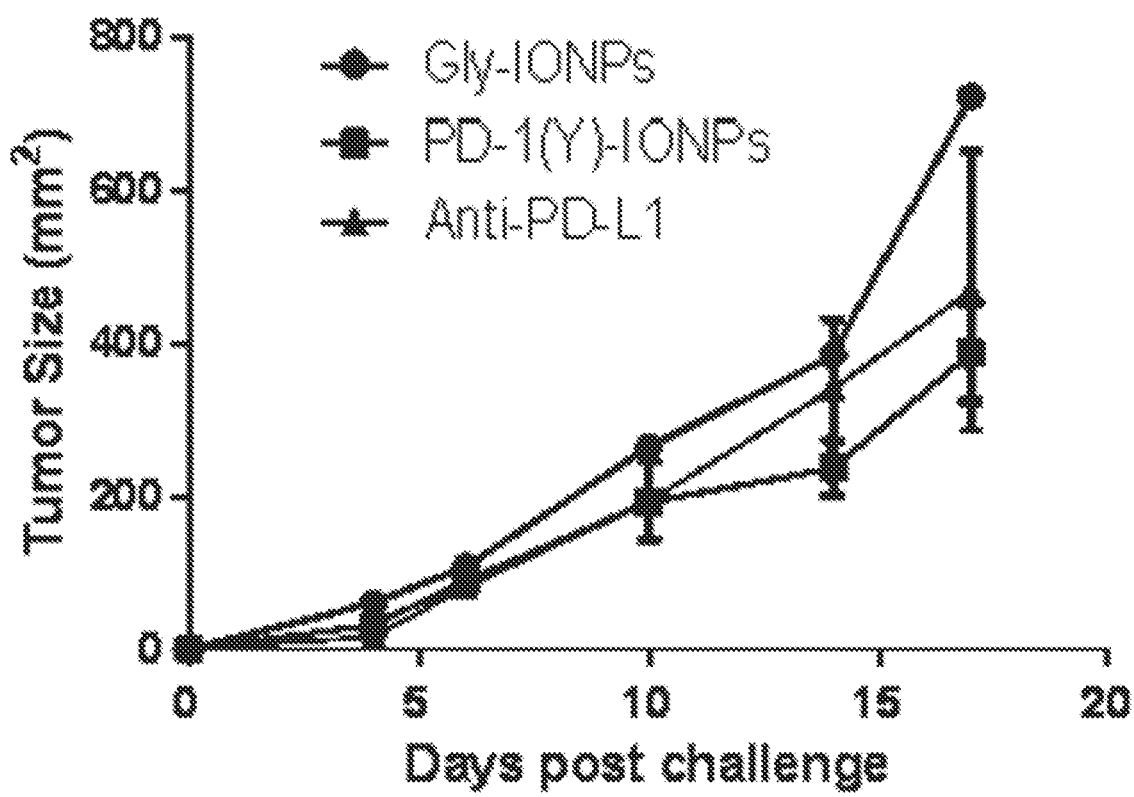
FIG. 7B shows data on tumor growth curves during treatment.
Figure 7C:
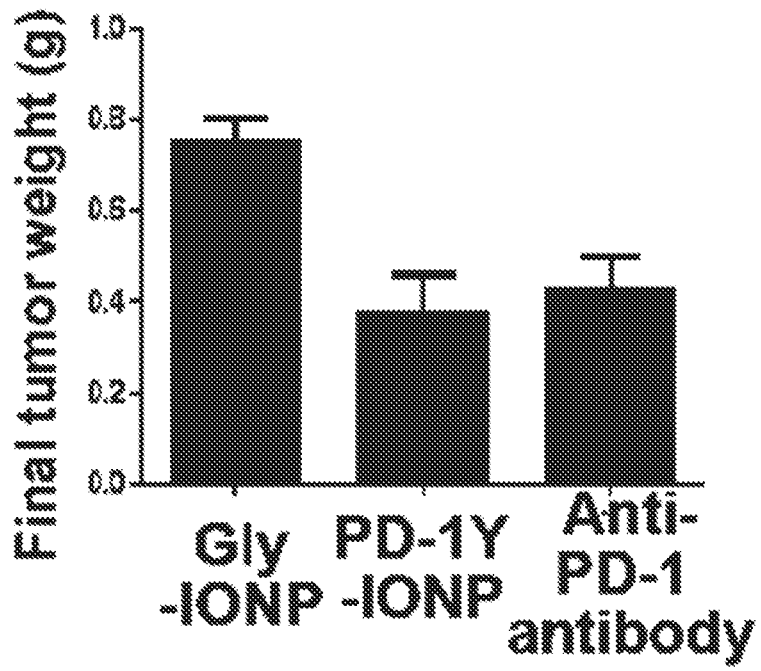
FIG. 7C shows data on mean tumor weight of each treatment group.

In Vivo Delivery of PD-1 Peptide Conjugated IONPs Inhibited the Growth of s.c. Pancreatic Tumors in the KC Cell Derived Transgenic Pancreatic Tumor Model To determine whether targeted delivery of PD-1 like peptide conjugated IONPs into tumor tissues can block PD-L1 immune checkpoint and produces an anti-tumor effect, the effect of systemic delivery of the PD-1Y-IONPs and an anti-mouse PD-L1 antibody was compared on the growth of the KC tumors injected s.c. into Kras wild type mice (FIG. 7A). Following four injections, there was no apparent body weight change and other symptoms of systemic toxicity. Significant inhibition of tumor growth was found in mice treated with PD-1Y-IONP or anti-PD-L1 antibody compared to non-targeted Gly-IONP control ($p<0.05$) (FIGS. 7B and C).

Pancreatic Cancer Specific T Cell Cyto-Toxicity in the KC Mouse Pancreatic Cancer Model To determine if tumor specific T cell response could be activated by targeted delivery of PD-1-IONPs, splenocytes from the orthotopic KC tumor bearing mice that received three i.p. deliveries of PD-1 Lin-IONP or PD-1 Y-IONP were collected. A CD3 positive T cell population was isolated using magnetic beads and then added to tissue culture plates with KC cells at a ratio of 1 tumor cell to 10 T cells. Following 72 hours co-culture, alarmaBlue™ cell proliferation was performed. There was a significant decrease in cell viability in KC cells incubated with T cells from the mice treated with PD-1Y-IONP, compared with no treatment control or treated with PD-1 Lin-IONP (FIG. 8).

The Combination of uPAR Targeted Delivery of Theranostic IONPs with Immune Check Point Blocking Using an Anti-PD-L Antibody Current clinical trials using therapeutic antibodies to block PD-1/PD-L1 failed to show a good therapeutic effect in pancreatic cancer patients, which is thought due to a low immunogenicity of pancreatic cancer tissues and presence of a dense tumor stromal barrier that prevents efficient delivery of antibodies into tumors blocking infiltration of T cells into the tumor tissues. Therefore, a combination therapy with targeted theranostic nanoparticles carrying chemotherapy agents has the potential to break tumor stromal barrier for improved delivery of PD-1L blocking agents. Delivery of nanoparticles into tumor tissue also promotes infiltration of antigen presenting cells into tumor center increasing the TIL cell population.

Figure 9A:
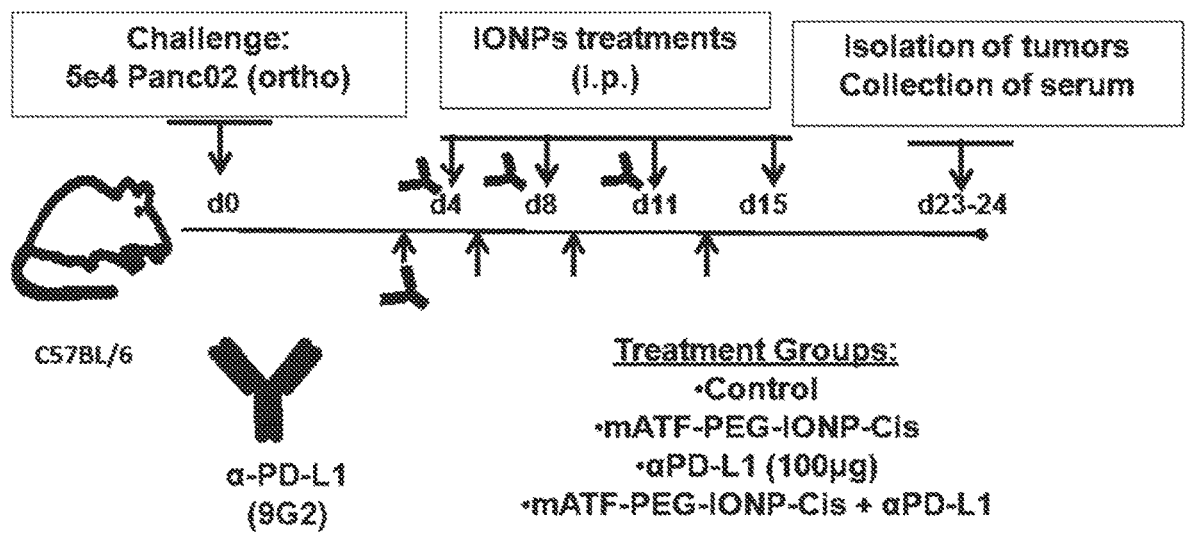
FIG. 9A shows an illustration of a uPAR targeted ATF-IONP-Cisplatin treatment protocol. The combination of uPAR-targeted delivery of theranostic IONPs with immune checkpoint blocking with an anti-PD-L antibody is used to enhance therapeutic responses in the Panc02 mouse pancreatic tumor model.
Figure 9B:
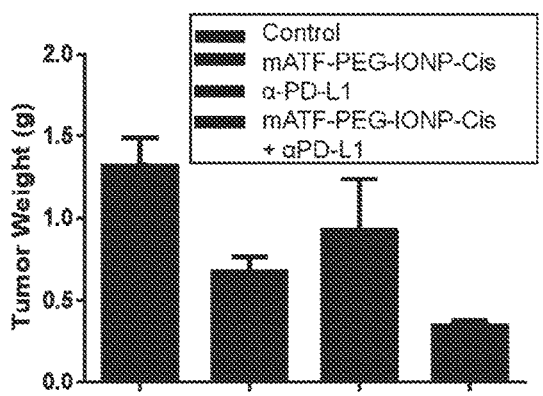
FIG. 9B shows data on mean tumor weight of each treatment group following four treatments.
Figure 9C:
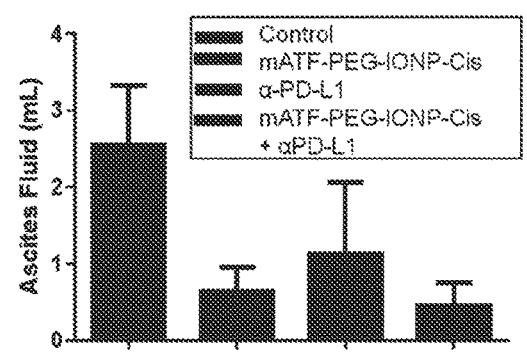
FIG. 9C shows data on mean volume of ascites in tumor bearing mice following different treatments.

The feasibility of a combination therapy was evaluated using an anti-mouse PD-L1 monoclonal antibody (BioX cell) in combination with uPAR-targeted ATF peptide conjugated IONP carrying cisplatin in the orthotopic Panc02 pancreatic tumor model in C57/B6 mice. Following four i.p. deliveries of mouse (m)ATF-IONP-cisplatin (5 mg/kg Cisplatin dose equivalent IONPs), control nanoparticles or antibodies, significant tumor growth inhibition was found in the tumor bearing mice that received mATF-IONP-cisplatin alone or mATF-IONP-cisplatin and the anti-PD-L1 antibody. The combination of mATF-IONP-cisplatin with anti-PD-L1 antibody showed enhanced therapeutic effect in Panc02 tumors. There was also significant reduction in the amount of ascites produced in the mice (FIG. 9A-C).

| Treatments | Avg Tumor Growth Inhibition (%) | Avg Ascites Fluid Inhibition (%) |
| --- | --- | --- |
| mATF-PEG-IONP-Cis | 49.1 | 74.5 |
| αPD-L1 | 29.9 | 55.6 |
| mATF-PEG-IONP-Cis + αPD-L1 | 73.4 | 81.7 |

Levels of CD4 or CD8+TIL cells were analyzed in the tumors after treatment. The combination therapy increased the levels of CD4 and CD8 T cells in tumors. Therefore, results of this study showed that the combination of targeted therapy using a nanoparticle drug carrier with targeted delivery of PD-L1 blocking nanoparticles is a promising approach for the development of effective cancer therapeutic agents.

Targeted Delivery of IONPs and Theranostic IONPs into Tumors Induces Immune Cell Infiltration for Enhanced Tumor Specific T Cell Response Immune therapy has not shown good responses in clinical trials for the treatment of pancreatic cancer. One of the potential mechanisms is thought to be the presence of tumor stromal barriers that limit delivery of therapeutic antibodies into tumor cell nest. Immunosuppressive cytokines also create a biological barrier for immune cells and immune function. It has also been shown that human pancreatic cancer tissues lack cytotoxic T cells. Additionally, pancreatic cancer has a low immunogenicity compared to other cancer types. It is important to combine cytotoxic agents to destroy tumor cells and release potentially immunogenic mutant proteins.

Figure 10:
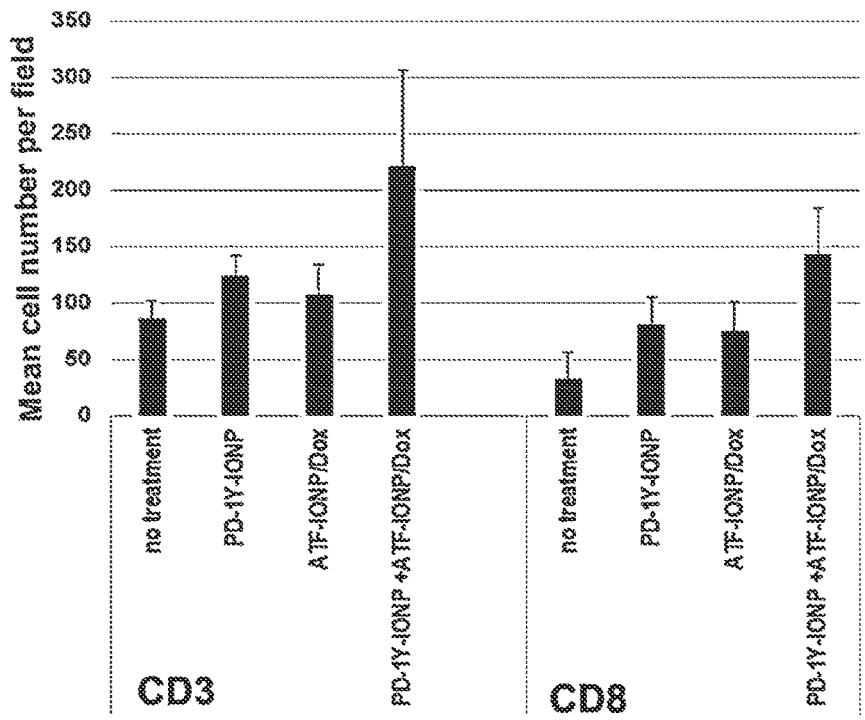
FIG. 10 shows data indicating targeted delivery of theranostic IONPs into tumors promoted infiltration of CD8+ cytotoxic T cells into pancreatic tumor tissues. Pdx1-Cre; LSL-K-rasG12D (KC) mouse pancreatic cancer cell line derived orthotopic tumors were used. Immunofluorescence labeling of CD3 and CD8+ T cells was done. Tumor bearing mice received 4×i.v. deliveries of the nanoparticles PD-1Y-IONP and/or AFTmmp14-IONP-Dox. Bar figure shows quantification of CD3 and CD8 cells in tumor tissue sections. Four to six tissue sections were examined for each mouse group.

Studies indicate that targeted delivery of theranostic IONPs into pancreatic cancer tissue promoted infiltration of immune cells into the tumor center. Four systemic deliveries of uPAR targeted PD1Y-IONP, ATFmmp14-IONP-Doxs, or the combination of both nanoparticles resulted in a high level of nanoparticle accumulation in pancreatic tumors in the Kras transgenic mouse model. However, NIR signal was not detectable in the tumor tissue section from NIR 830 dye labeled non-targeted IONP treated mouse. Those frozen tissue sections were further labeled with antibodies against CD3 and CD8. CD4 was not used since it also reacts with a subpopulation of macrophages. Immunofluorescence labeling using antibodies for total T cell (CD3) or cytotoxic T cell (CD8) revealed that KPC tumor tissues have an intermediate level of CD3+ T cells but lack CD8+ cytotoxic T cells. These CD3+/CD8− T cells are likely to be CD4 T cells with a subpopulation of these cells being T suppressor cells. However, ATPmmp14-IONP-Dox treated tumor tissues had marked increases in CD8+ T cells that infiltrated into and surrounded ductal tumor cells. A high percentage of CD3+ T cells are also CD8+ cells, suggesting significant increase in the cytotoxic T cells in the tumor tissue. PD1Y-IONP treatment slightly increased CD3 and CD8+ T cells. ATPmmp14-IONP-Dox theranostic IONP or the combination of both IONPs treated tumors had marked increases in the CD8+ and CD3+ T cells (FIG. 10). The observed effect of modulating T cell populations in tumor tissues following targeted delivery of theranostic IONPs is very significant for improving the therapeutic response to anti-PD1/PDL-1 checkpoint medicated immunotherapy of pancreatic cancer.

The effect of targeted delivery of nanoparticles on promoting intratumoral infiltration of T cells has also been demonstrated in the Pdx1-Cre;LSL-K-rasG12D P53Trp53R (KPC) transgenic mouse pancreatic cancer model using another theranostic IONP. Systemic delivery of PD1Y, ATFmmp14 or dual ATFmmp14+PD1Y conjugated ultrafine IONPs (3.5 nm core) carrying SN38 (derivative of CPT-11) into the KPC mice led to targeted delivery into orthotopic pancreatic tumors that is detectable by optical imaging. Immunofluorescence labeling of tumor tissue sections revealed increased numbers of CD3 and CD8 T cells in the tumors.

Determination of PDL1 Targeted Delivery of HANP Polymeric Nanoparticles into Human Breast Cancer Tissue Derived Xenograft (PDX) Model.

To determine if the PD1Y peptide can be used for targeted delivery of other types of nanoparticles and for immunotherapy of different human tumors, PD1Y peptides were conjugated to HANP polymeric nanoparticles (150 nm). Systemic delivery of PD1Y-HANPs into a nude mice bearing human breast cancer tissue derived xenografts (PDX) led to the accumulation of the NIR 830 dye labeled HANP and allowed for optical imaging of breast tumors in mice. Ex vivo organ imaging showed an optical signal in the tumor. In normal organs, signal was only found in the liver and kidney.

Figure 11A:
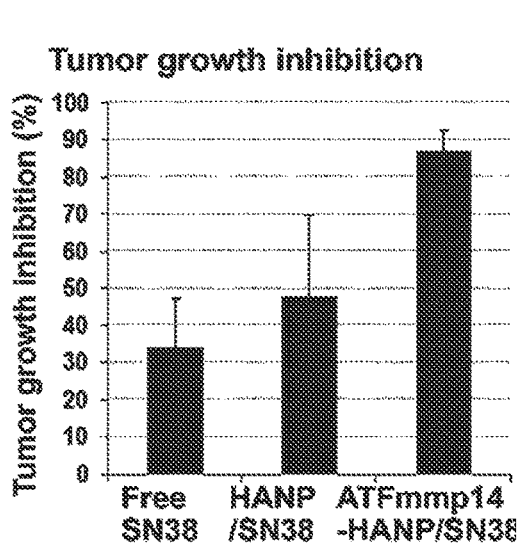
FIG. 11A shows data indicating an effect of targeted therapy on pancreatic cancer by systemic delivery of stroma breaking ATFmmp14-HANP/SN38 in a human pancreatic cancer PDX model. The percentage of tumor growth inhibition following five weekly i.v. injections of 5 mg/Kg SN38 equivalent dose of free SN38 or HANP/SN38. PDX tumor weight of the no treatment control group was used as a reference. Significant tumor growth inhibition was found in the mouse group treated with ATFmmp14-HANP/SN38 compared to free SN38 and HANP/SN38 treated groups.
Figure 11B:
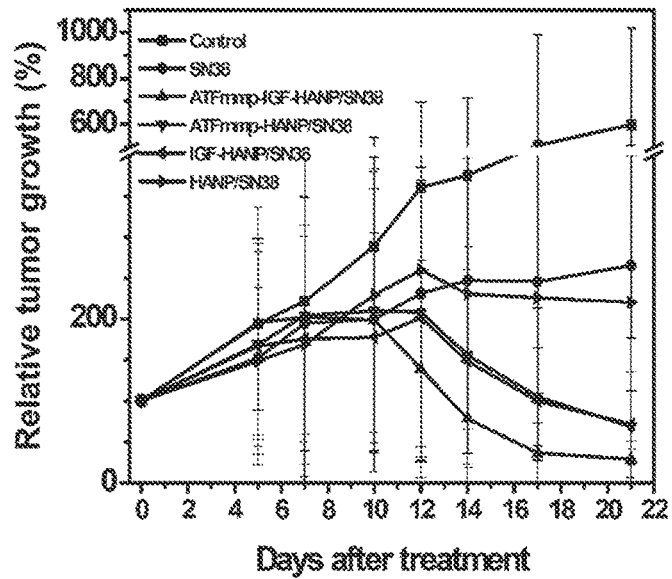
FIG. 11B shows data on targeted therapy of drug resistant breast cancer following systemic delivery of ATFmmp14 conjugated HANP carrying SN38. Human breast cancer patient tissue derived xenograft models were used for the study including ER positive and triple negative breast cancer. The figure shows the tumor growth inhibition in the ER positive breast cancer PDX model.
Figure 12:
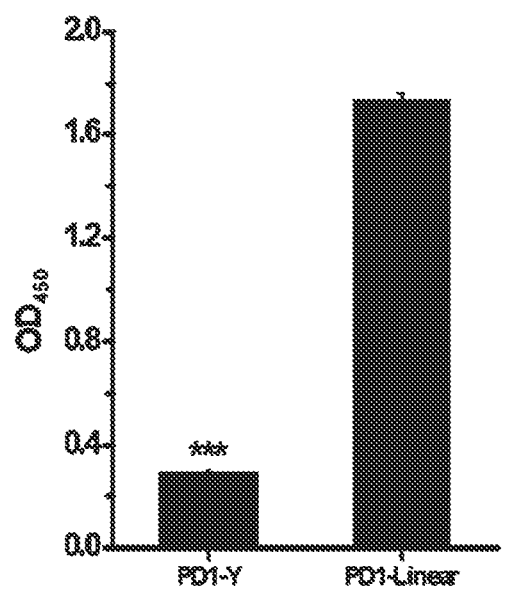
FIG. 12 shows analysis of binding affinity of two PD1 peptides that mimetic a specific interaction site on PD-L1.

ATFmmp14-HANP/SN38 Treatment Improved Therapeutic Effects in Both Pancreatic and Breast Cancer Using PDX Tumor Models To increasing drug delivery into tumors after systemic administration, Urokinase plasminogen activator receptor (uPAR) fused matrix metalloproteinase 14 was conjugated onto a HANP/SN38 complex. ATFmmp14-HANP/SN38 complex has great potential in improving cancer therapeutic effects. Efficacy studies were carried out using ATFmmp14-HANP/SN38 in a human pancreatic cancer patient tissue derived xenograft (PDX) in nude mice. SN38 (7-ethyl-10-hydroxy-camptothecin) is an active metabolite of the chemotherapy drug, irinotecan. Systemic delivery of ATFmmp14-HANP/SN38 significantly inhibited the growth of orthotopic tumors in the human pancreatic PDX tumor model (FIG. 11A). Induction of a high level of apoptotic cell death and significant reduction of the level of stromal fibroblasts were detected in tumor tissues following the targeted therapy, compared with control groups. The HANP/SN38 complex more efficiently ablates pancreatic cancer growth (88%) with ATFmmp14, while HANP/SN38 without ATFmmp14 only showed less than 50% tumor growth inhibition, suggesting that breaking stroma barrier is helpful for improving cancer therapy responses. The effect of the targeted HANP was further evaluated in human breast cancer PDX models. Significant tumor growth inhibition was also found in those PDX models derived from both ER+ and triple negative breast cancer patients (FIG. 11B).

```
                              SEQUENCE LISTING

Sequence total quantity: 34
SEQ ID NO: 1            moltype = AA   length = 288
FEATURE                 Location/Qualifiers
source                  1..288
                        mol_type = protein
                        organism = synthetic construct
SEQUENCE: 1
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFS VDYGELDFQW REKTPEPPVP   240
CVPEQTEYAT IVFPSGMGTS SPARRGSADG PRSAQPLRPE DGHCSWPL               288

SEQ ID NO: 2            moltype = AA   length = 35
FEATURE                 Location/Qualifiers
source                  1..35
                        mol_type = protein
                        organism = synthetic construct
SEQUENCE: 2
NWNRLSPSNQ TEKQAAPHHH HCGAISLHPK AKIEE                               35

SEQ ID NO: 3            moltype = AA   length = 37
FEATURE                 Location/Qualifiers
source                  1..37
                        mol_type = protein
                        organism = synthetic construct
SEQUENCE: 3
NWNRLSPSNQ TEKQAACGAI SLHPKAKIEE SPGHHHH                             37

SEQ ID NO: 4            moltype = AA   length = 4
FEATURE                 Location/Qualifiers
source                  1..4
                        mol_type = protein
                        organism = synthetic construct
SEQUENCE: 4
GFLG                                                                  4

SEQ ID NO: 5            moltype = AA   length = 135
FEATURE                 Location/Qualifiers
source                  1..135
                        mol_type = protein
                        organism = synthetic construct
SEQUENCE: 5
SNELHQVPSN CDCLNGGTCV SNKYFSNIHW CNCPKKFGGQ HCEIDKSKTC YEGNGHFYRG    60
KASTDTMGRP CLPWNSATVL QQTYHAHRSD ALQLGLGKHN YCRNPDNRRR PWCYVQVGLK   120
PLVQECMVHD CADGK                                                   135

SEQ ID NO: 6            moltype = AA   length = 68
FEATURE                 Location/Qualifiers
source                  1..68
                        mol_type = protein
                        organism = synthetic construct
SEQUENCE: 6
SNELHQVPSN CDCLNGGTCV SNKYFSNIHW CNCPKKFGGQ HCEIDKSKTC YEGNGHFYRG    60
KASTDTMG                                                             68

SEQ ID NO: 7            moltype = AA   length = 280
FEATURE                 Location/Qualifiers
source                  1..280
                        mol_type = protein
                        organism = synthetic construct
SEQUENCE: 7
MSNELHQVPS NCDCLNGGTC VSNKYFSNIH WCNCPKKFGG QHCEIDKSKT CYEGNGHFYR    60
GKASTDGAPI QGLKWQHNEI TFCIQNYTPK VGEYATYEAI RKAFRVWESA TPLRFREVPY   120
AYIREGHEKQ ADIMIFFAEG FHGDSTPFDG EGGFLAHAYF PGPNIGGDTH FDSAEPWTVR   180
NEDLNGNDIF LVAVHELGHA LGLEHSSDPS AIMAPFYQWM DTENFVLPDD DRRGIQQLYG   240
GESGFPTKMP PQPRTTSRPS VPDKPKNPTY GPNIHHHHHH                         280

SEQ ID NO: 8            moltype = AA   length = 17
FEATURE                 Location/Qualifiers
source                  1..17
                        mol_type = protein
```

```
                                -continued organism = synthetic construct
SEQUENCE: 8
NWNRLSPSNQ TEKQAAP                                                        17

SEQ ID NO: 9           moltype = AA   length = 14
FEATURE                Location/Qualifiers
source                 1..14
                       mol_type = protein
                       organism = synthetic construct
SEQUENCE: 9
CGAISLHPKA KIEE                                                           14

SEQ ID NO: 10          moltype = AA   length = 30
FEATURE                Location/Qualifiers
source                 1..30
                       mol_type = protein
                       organism = synthetic construct
SEQUENCE: 10
ESFVLNWYRM SPSNQTDKLA AFPEDRSQPG                                          30

SEQ ID NO: 11          moltype = AA   length = 38
FEATURE                Location/Qualifiers
source                 1..38
                       mol_type = protein
                       organism = synthetic construct
SEQUENCE: 11
PNGRDFHMSV VRARRNDSGT CGAISLAPKA QIKESLRA                                 38

SEQ ID NO: 12          moltype = AA   length = 16
FEATURE                Location/Qualifiers
source                 1..16
                       mol_type = protein
                       organism = synthetic construct
SEQUENCE: 12
NWYRMSPSNQ TDKLAA                                                         16

SEQ ID NO: 13          moltype = AA   length = 14
FEATURE                Location/Qualifiers
source                 1..14
                       mol_type = protein
                       organism = synthetic construct
SEQUENCE: 13
CGAISLAPKA QIKE                                                           14

SEQ ID NO: 14          moltype = AA   length = 17
FEATURE                Location/Qualifiers
source                 1..17
                       mol_type = protein
                       organism = synthetic construct
SEQUENCE: 14
NWNRMSPSNQ TEKQAAP                                                        17

SEQ ID NO: 15          moltype = AA   length = 17
FEATURE                Location/Qualifiers
source                 1..17
                       mol_type = protein
                       organism = synthetic construct
SEQUENCE: 15
NWNRMSPSNQ TDKQAAP                                                        17

SEQ ID NO: 16          moltype = AA   length = 17
FEATURE                Location/Qualifiers
source                 1..17
                       mol_type = protein
                       organism = synthetic construct
SEQUENCE: 16
NWNRMSPSNQ TDKLAAP                                                        17

SEQ ID NO: 17          moltype = AA   length = 17
FEATURE                Location/Qualifiers
source                 1..17
                       mol_type = protein
                       organism = synthetic construct
SEQUENCE: 17
NWNRLSPSNQ TEKLAAP                                                        17

SEQ ID NO: 18          moltype = AA   length = 17
FEATURE                Location/Qualifiers
source                 1..17
```

```
                            mol_type = protein
                            organism = synthetic construct
SEQUENCE: 18
NWNRLSPSNQ TDKLAAP                                                          17

SEQ ID NO: 19               moltype = AA   length = 17
FEATURE                     Location/Qualifiers
source                      1..17
                            mol_type = protein
                            organism = synthetic construct
SEQUENCE: 19
NWYRMSPSNQ TEKQAAP                                                          17

SEQ ID NO: 20               moltype = AA   length = 17
FEATURE                     Location/Qualifiers
source                      1..17
                            mol_type = protein
                            organism = synthetic construct
SEQUENCE: 20
NWYRMSPSNQ TDKQAAP                                                          17

SEQ ID NO: 21               moltype = AA   length = 17
FEATURE                     Location/Qualifiers
source                      1..17
                            mol_type = protein
                            organism = synthetic construct
SEQUENCE: 21
NWYRMSPSNQ TDKLAAP                                                          17

SEQ ID NO: 22               moltype = AA   length = 17
FEATURE                     Location/Qualifiers
source                      1..17
                            mol_type = protein
                            organism = synthetic construct
SEQUENCE: 22
NWYRLSPSNQ TEKLAAP                                                          17

SEQ ID NO: 23               moltype = AA   length = 17
FEATURE                     Location/Qualifiers
source                      1..17
                            mol_type = protein
                            organism = synthetic construct
SEQUENCE: 23
NWYRLSPSNQ TDKLAAP                                                          17

SEQ ID NO: 24               moltype = AA   length = 14
FEATURE                     Location/Qualifiers
source                      1..14
                            mol_type = protein
                            organism = synthetic construct
SEQUENCE: 24
CGAISLAPKA KIEE                                                             14

SEQ ID NO: 25               moltype = AA   length = 14
FEATURE                     Location/Qualifiers
source                      1..14
                            mol_type = protein
                            organism = synthetic construct
SEQUENCE: 25
CGAISLAPKA QIEE                                                             14

SEQ ID NO: 26               moltype = AA   length = 6
FEATURE                     Location/Qualifiers
source                      1..6
                            mol_type = protein
                            organism = synthetic construct
SEQUENCE: 26
GGGGGG                                                                       6

SEQ ID NO: 27               moltype = AA   length = 14
FEATURE                     Location/Qualifiers
source                      1..14
                            mol_type = protein
                            organism = synthetic construct
SEQUENCE: 27
CGAISLHPKA KIKE                                                             14

SEQ ID NO: 28               moltype = AA   length = 14
FEATURE                     Location/Qualifiers
```

```
source                  1..14
                        mol_type = protein
                        organism = synthetic construct
SEQUENCE: 28
CGAISLHPKA QIKE                                                        14

SEQ ID NO: 29           moltype = AA  length = 35
FEATURE                 Location/Qualifiers
source                  1..35
                        mol_type = protein
                        organism = synthetic construct
SEQUENCE: 29
NWYRMSPSNQ TDKLAAPXXX XCGAISLAPK AQIKE                                 35

SEQ ID NO: 30           moltype = AA  length = 34
FEATURE                 Location/Qualifiers
source                  1..34
                        mol_type = protein
                        organism = synthetic construct
SEQUENCE: 30
NWYRMSPSNQ TDKLAAPXXX CGAISLAPKA QIKE                                  34

SEQ ID NO: 31           moltype = AA  length = 36
FEATURE                 Location/Qualifiers
source                  1..36
                        mol_type = protein
                        organism = synthetic construct
SEQUENCE: 31
NWYRMSPSNQ TDKLAAPXXX XXCGAISLAP KAQIKE                                36

SEQ ID NO: 32           moltype = AA  length = 5
FEATURE                 Location/Qualifiers
source                  1..5
                        mol_type = protein
                        organism = synthetic construct
SEQUENCE: 32
GGGGT                                                                  5

SEQ ID NO: 33           moltype = AA  length = 6
FEATURE                 Location/Qualifiers
source                  1..6
                        mol_type = protein
                        organism = synthetic construct
SEQUENCE: 33
GGGPPP                                                                 6

SEQ ID NO: 34           moltype = AA  length = 7
FEATURE                 Location/Qualifiers
source                  1..7
                        mol_type = protein
                        organism = synthetic construct
SEQUENCE: 34
GGGAPPP                                                                7
```

The invention claimed is:

1. A peptide comprising NWNRLSPSNQTEKQ-AAPHHHHCGAISLHPKAKIEE (SEQ ID NO: 2).

2. A nucleic acid comprising a sequence encoding the peptide of claim 1.

3. A vector comprising a nucleic acid of claim 2.

4. A cell comprising a vector of claim 3.

* * * * *